US010295485B2

(12) United States Patent
Yun et al.

(10) Patent No.: US 10,295,485 B2
(45) Date of Patent: May 21, 2019

(54) X-RAY TRANSMISSION SPECTROMETER SYSTEM

(71) Applicant: Sigray, Inc., Concord, CA (US)

(72) Inventors: Wenbing Yun, Walnut Creek, CA (US); Srivatsan Seshadri, Pleasanton, CA (US); Janos Kirz, Berkeley, CA (US); Sylvia Jia Yun Lewis, San Francisco, CA (US)

(73) Assignee: Sigray, Inc., Concord, CA (US)

(*) Notice: Subject to any disclaimer, the term of this patent is extended or adjusted under 35 U.S.C. 154(b) by 3 days.

(21) Appl. No.: 15/663,831

(22) Filed: Jul. 31, 2017

(65) Prior Publication Data

US 2017/0336334 A1 Nov. 23, 2017

Related U.S. Application Data

(63) Continuation-in-part of application No. 15/431,786, filed on Feb. 14, 2017, which is a continuation-in-part (Continued)

(51) Int. Cl.
*G01N 23/223* (2006.01)
*G01N 23/207* (2018.01)
(Continued)

(52) U.S. Cl.
CPC ....... *G01N 23/2076* (2013.01); *G01N 23/087* (2013.01); *G01N 23/223* (2013.01);
(Continued)

(58) Field of Classification Search
CPC .. G01N 2/2076; G01N 23/087; G01N 23/223; G01N 2223/04; G01N 2223/045;
(Continued)

(56) References Cited

U.S. PATENT DOCUMENTS 1,203,495 A 10/1916 Coolidge
1,211,092 A 1/1917 Coolidge
(Continued)

FOREIGN PATENT DOCUMENTS

CN 102124537 A 7/2011
EP 0432568 6/1991
(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
(Continued)

*Primary Examiner* — Courtney Thomas
(74) *Attorney, Agent, or Firm* — Knobbe, Martens, Olson & Bear, LLP

(57) ABSTRACT

An x-ray transmission spectrometer system to be used with a compact x-ray source to measure x-ray absorption with both high spatial and high spectral resolution. The spectrometer system comprises a compact high brightness x-ray source, an optical system with a low pass spectral filter property to focus the x-rays through an object to be examined, and a spectrometer comprising a crystal analyzer (and, in some embodiments, a mosaic crystal) to disperse the transmitted beam, and in some instances an array detector. The high brightness/high flux x-ray source may have a take-off angle between 0 and 15 degrees, and be coupled to an optical system that collects and focuses the high flux x-rays to micron-scale spots, leading to high flux density. The x-ray optical system may also act as a "low-pass" filter, allowing a predetermined bandwidth of x-rays to be observed at one time while excluding the higher harmonics.

22 Claims, 15 Drawing Sheets

Related U.S. Application Data of application No. 15/269,855, filed on Sep. 19, 2016, now Pat. No. 9,570,265, and a continuation-in-part of application No. 15/166,274, filed on May 27, 2016, now Pat. No. 10,269,528, which is a continuation-in-part of application No. 14/636,994, filed on Mar. 3, 2015, now Pat. No. 9,448,190, said application No. 15/431,786 is a continuation-in-part of application No. 14/544,191, filed on Dec. 5, 2014, now Pat. No. 9,449,781.

(60) Provisional application No. 62/117,062, filed on Feb. 17, 2015, provisional application No. 61/912,478, filed on Dec. 5, 2013, provisional application No. 61/912,486, filed on Dec. 5, 2013, provisional application No. 61/946,475, filed on Feb. 28, 2014, provisional application No. 62/008,856, filed on Jun. 6, 2014, provisional application No. 62/086,132, filed on Dec. 1, 2014.

(51) Int. Cl.
*G01N 23/087* (2018.01)
*G21K 1/06* (2006.01)
*H01J 35/08* (2006.01)
*H01J 35/14* (2006.01)
*H01J 35/18* (2006.01)

(52) U.S. Cl.
CPC ............. *G21K 1/06* (2013.01); *G21K 1/067* (2013.01); *H01J 35/08* (2013.01); *H01J 35/14* (2013.01); *H01J 35/18* (2013.01); *G01N 2223/04* (2013.01); *G01N 2223/045* (2013.01); *G01N 2223/0568* (2013.01); *G21K 2201/064* (2013.01); *H01J 2235/081* (2013.01); *H01J 2235/086* (2013.01)

(58) Field of Classification Search
CPC .. G01N 2223/0568; G21K 1/06; G21K 1/067; G21K 2201/064; H01J 35/08; H01J 35/14; H01J 35/18
See application file for complete search history.

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,266,138 A | 5/1981 | Nelson et al. |
| 4,277,112 A | 7/1981 | Heshmat |
| 4,426,718 A | 1/1984 | Hayashi et al. |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,768,339 A | 6/1998 | O'Hara |
| 5,772,903 A | 6/1998 | Hirsch |
| 5,778,039 A * | 7/1998 | Hossain ........... G01N 23/20008 378/44 |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |

(56) References Cited

U.S. PATENT DOCUMENTS

| | | | |
|---|---|---|---|
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 * | 5/2011 | Brons ............. G01N 23/223 378/44 |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,041,004 B2 | 10/2011 | David |
| 8,036,341 B2 | 11/2011 | Lee |
| 8,068,579 B1 | 11/2011 | Yun et al. |
| 8,073,099 B2 | 12/2011 | Niu et al. |
| 8,094,784 B2 | 1/2012 | Morton |
| 8,139,716 B2 | 3/2012 | Okunuki et al. |
| 8,184,771 B2 | 5/2012 | Murakoshi |
| 8,208,603 B2 | 6/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,543,109 B2 | 1/2017 | Yun et al. |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,823,203 B2 | 11/2017 | Yun et al. |
| 9,874,531 B2 | 1/2018 | Yun et al. |
| 9,939,392 B2 | 4/2018 | Wen |
| 2001/0006413 A1 | 7/2001 | Burghoorn |
| 2002/0085676 A1 | 7/2002 | Snyder |
| 2003/0142790 A1 | 1/2003 | Zhou et al. |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc et al. |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |

(56) References Cited

U.S. PATENT DOCUMENTS

| | | |
|---|---|---|
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn et al. |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0261442 A1 | 9/2017 | Yun et al. |
| 2017/0336334 A1 | 11/2017 | Yun et al. |
| 2018/0144901 A1 | 5/2018 | Yun et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H07-056000 | 3/1995 |
| JP | 2000-306533 | 11/2000 |
| JP | 2007-265981 | 10/2007 |
| JP | 2007-311185 | 11/2007 |
| JP | 2008-200359 | 4/2008 |
| JP | 2008-197495 | 8/2008 |
| JP | 2011-029072 | 2/2011 |
| JP | 2012-187341 | 10/2012 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/204850 | 11/2017 |
| WO | WO 2017/213996 | 12/2017 |

OTHER PUBLICATIONS

"Element Six CVD Diamond Handbook" (Element Six, Luxembourg, 2015).

"High performance benchtop EDXRF spectrometer with Windows® software," published by: Rigaku Corp., Tokyo, Japan; 2017.

"Monochromatic Doubly Curved Crystal Optics," published by: X-Ray Optical Systems, Inc. (XOS), East Greenbush, NY; 2017.

"Optics and Detectors," Section 4 of XS-Ray Data Booklet, 3rd Ed., A.C. Thompson ed. (Lawrence Berkeley Nat'l Lab, Berkeley, CA, 2009).

"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.

"Science and Technology of Future Light Sources", Arthur L. Robinson (LBNL) and Brad Plummer (SLAG), eds. Report Nos.

(56) References Cited

OTHER PUBLICATIONS

ANL-08/39 / BNL-81895-2008 / LBNL-1090E-2009 / SLAC-R-917 (Lawrence Berkeley Nat'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nat'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagen PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628- 635 (9 pages). Aug. 6, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.

(56) References Cited

OTHER PUBLICATIONS

Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.

Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.

(56) References Cited

OTHER PUBLICATIONS

Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factory, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.

Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_ Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.

(56) References Cited

OTHER PUBLICATIONS

Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, "Ueber eine neue Art von Strahlen (Wurzburg Verlag, Warzburg, Germany, 1896) also, in English, On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Université Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentation s/Strueder.pdf>.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).
Takahama, "RADspeed safire Digital General Radiography System Equipped with New Direct-Conversion FPD," Medical Now, No. 62 (2007).
Takeda et al., "Differential Phase X-ray Imaging Microscopy with X-ray Talbot Interferometer." Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science no. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.

(56) References Cited

OTHER PUBLICATIONS

Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Fabrication of Diamond Microstructures by Using Dry and Wet Etching Methods", Plasma Science and Technology vol. 15(6) (Jun. 2013), pp. 552-554.

* cited by examiner

X-RAY TRANSMISSION SPECTROMETER SYSTEM

CROSS-REFERENCE TO RELATED APPLICATIONS

Patent Application is a Continuation-in-Part of U.S. patent application Ser. No. 15/431,786, filed Feb. 14, 2017, which in turn is a Continuation-in-Part of U.S. patent application Ser. No. 15/269,855, filed Sep. 19, 2016 now issued as U.S. Pat. No. 9,570,265, and is also a Continuation-in-Part of U.S. patent application Ser. No. 15/166,274, filed May 27, 2016, all of which are hereby incorporated by reference in their entirety. Additionally, U.S. patent application Ser. No. 15/269,855 is a Continuation-in-Part of U.S. patent application 14/544,191, filed Dec. 5, 2014 and now issued as U.S. Pat. No. 9,449,781, which is hereby incorporated by reference in its entirety, and which claims the benefit of U.S. Provisional Patent Application Nos. 61/912,478, filed on Dec. 5, 2013, 61/912,486, filed on Dec. 5, 2013, 61/946,475, filed on Feb. 28, 2014, and 62/008,856, filed on Jun. 6, 2014, all of which are incorporated herein by reference in their entirety. Application Ser. No. 15/269,855 is also a Continuation-in-Part of U.S. patent application Ser. No. 14/636,994, filed Mar. 3, 2015 and now issued as U.S. Pat. No. 9,448,190, which is hereby incorporated by reference in its entirety, and which in turn claims the benefit of U.S. Provisional Patent Application Nos. 62/008,856, filed Jun. 6, 2014; 62/086,132, filed Dec. 1, 2014, and 62/117,062, filed Feb. 17, 2015, all of which are incorporated herein by reference in their entirety.

BACKGROUND

Measurement of the x-ray absorption properties of a material near the ionization energy can reveal information about the chemical state of the elements of interest within a sample, revealing information such as oxidation state and coordination number.

X-ray absorption spectroscopy (XAS) measures the fraction of x-rays absorbed by an object as a function of x-ray energy over a predetermined narrow energy range. It is often carried out at synchrotron light sources because of their high brightness and energy tunability. Unfortunately, synchrotron based x-ray absorption spectroscopy systems have numerous accessibility limitations, such as long wait times to obtain proposal-based access, limited measurement time granted per user group, and logistic issues including the need for travel and shipment of special experiment.

Small laboratory-based x-ray absorption spectroscopy systems would provide easy access and full control, however the performance of laboratory XAS systems has been largely limited by a combination of many factors, including low brightness and flux of laboratory x-ray sources, low efficiency of the x-ray optic used, and low diffraction efficiency of the crystal analyzer associated with the use of high index reflections required for high energy resolution measurements due to the typically large x-ray source sizes of laboratory sources. Those limitations result in unacceptably long acquisition times (tens of hours) and/or poor energy resolution. As a result, there are few laboratory systems in use.

There is a need for a laboratory x-ray absorption spectroscopy system with high throughput that circumvents the limitations of prior laboratory XAS systems.

SUMMARY

The present technology, roughly described, is an x-ray absorption spectrometer usable with a compact x-ray source to measure x-ray transmission with high throughput, high spatial, and high spectral resolution. In some instances, the spectrometer includes an optical x-ray optic system which achromatically focuses x-rays emerging from the x-ray source to preserve the brightness of the x-ray source, also serves as a low-pass filter with a predetermined high-energy cut-off for the x-rays. One major advantage of the use of an x-ray optical system serving as low-pass focusing reflector is that the energy of the electrons of the x-ray source can be substantially higher than the predetermined high-energy cut-off, increasing the x-ray production efficiency to achieve high source brightness. This x-ray optical system can provide a point or a line focus that serves as the virtual source for x-rays in a spectrometer comprising of a crystal analyzer.

In some instances, a method for x-ray absorption spectroscopy by an x-ray optical system includes collecting x-rays received from a first x-ray source through an x-ray optical system. The x-ray optical system has low-pass spectral filter properties such that x-rays above a cut-off energy are reduced. A focused x-ray beam is produced by the x-ray optical system with a focus at a predetermined focal plane downstream of the x-ray optical system. The focused x-ray beam passes through a sample to be analyzed. The focused x-ray beam acts as a secondary source of diverging x-rays located at the focal plane. The diverging x-rays from the secondary source are received by an x-ray spectrometer having an x-ray wavelength dispersive element and an analyzer to analyze the spectrum of the dispersed x-rays.

DETAILED DESCRIPTION

Figure 1:
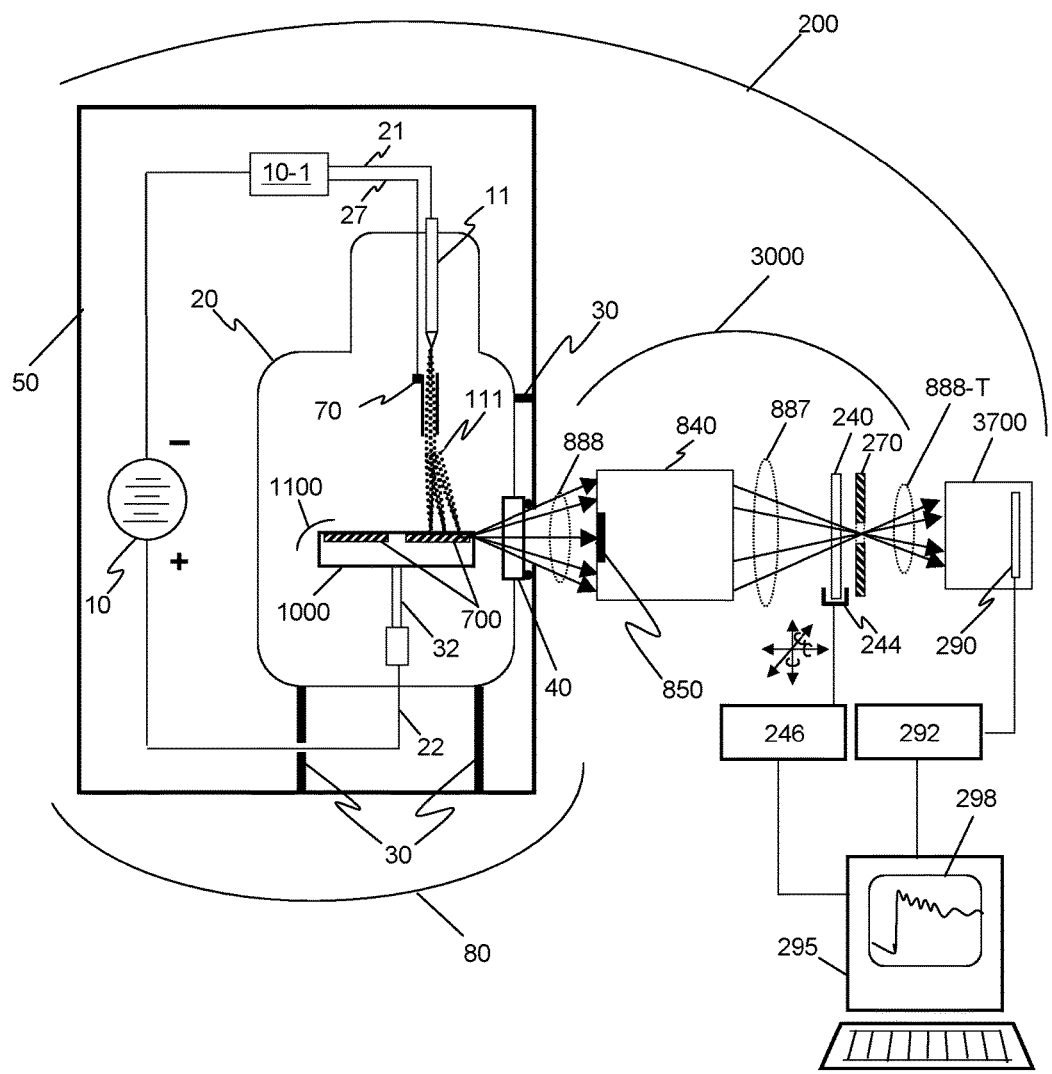
FIG. 1 illustrates a block diagram of an exemplary x-ray spectrometer system 200.

Instances of the present technology include an x-ray absorption spectrometer usable with a compact x-ray source (e.g., first source) to measure x-ray transmission with high throughput, high spatial, and high spectral resolution. In some instances, the spectrometer includes an x-ray optical system which achromatically focuses x-rays emerging from the x-ray source that preserves the brightness of the x-ray source and also serves as a low-pass filter with a predetermined high-energy cut-off for the x-rays. One major advantage of the use of an x-ray optical system serving as low-pass focusing reflector is that the accelerating voltage of the electrons of the x-ray source can be substantially higher than the predetermined high-energy cut-off, increasing the x-ray production efficiency to achieve high source brightness. This optical system can provide a point or a line focus that serves as the virtual source for x-rays in a spectrometer that includes of a crystal analyzer.

The x-ray optical elements in the train may include paraboloid optics, ellipsoidal optics, polycapillary optics, or various types of Wolter optics, Kirkpatrick-Baez mirrors or multilayers suitably graded and systems comprising combinations thereof. The high collection and focusing efficiency achievable using these optical elements helps achieve high flux density in tightly focused spots.

In some embodiments, the higher brightness compact x-ray source is achieved in part through the use of novel x-ray targets used in generating x-rays from electron beam bombardment. These x-ray target configurations may include a number of microstructures of one or more selected x-ray generating materials fabricated in close thermal contact with (such as embedded in or buried in) a substrate with high thermal conductivity, such that the heat is more efficiently drawn out of the x-ray generating material. This in turn allows bombardment of the x-ray generating material with higher electron density and/or higher energy electrons, which leads to greater x-ray brightness and greater x-ray flux.

An object to be examined in transmission is placed in the x-ray beam, and an aperture is placed at the point or line of focus to selectively pass the transmitted x-rays while restricting the widely radiated x-ray fluorescence and any scattered radiation that may exist. The object may be translated in x- and y-axes to allow a 2-D "map" of the transmission spectrum to be collected.

The aperture placed at the point or line of focus becomes the "source" (often referred to as the virtual source or second source) for a second x-ray optical system (the spectrometer) designed to disperse x-rays emerging from the aperture. This second system uses diffractive analyzer crystals to diffract x-rays of different energies onto an array detector, aligned so that different pixels of the detector correspond to different x-ray energies.

In some embodiments, an additional beam stop may be placed after the aperture to block the directly transmitted beam, but allow x-ray fluorescence emitted by the object to enter the spectrometer and be spectroscopically analyzed.

The present x-ray optical system may have several advantages. One or more optics of the x-ray optical system can be used as a low pass filter to cut out and/or reduce the energy of at least a portion of the x-rays provided by an x-ray source to provide a second source for directing at a target. Additionally, the x-ray optical system may allow selection of one of a plurality of optics. This interchangeability of sources based on a selected optic provides different spectrums that can be optimized for different tasks.

The present x-ray optical system also provides for high spatial resolution. The present system can interrogate a sample and raster scan the sample at a spatial resolution of 10 microns, for example. This degree of spatial resolution is much stronger than prior systems, which for example provide resolution at a millimeter level.

The present x-ray optical system further provides a sample holder or mount that can include multiple samples without requiring a door of the system to be opened, and wherein each sample can be positioned at a distance from the source other than at or close to the source. In some instances, the mount can receive one or more of a plurality of samples and positions at least one sample in the focused x-ray beam for analysis. This variable sample positioning is better suited to changes in temperature and/or the environment and therefore provides for more accurate analysis of the sample. Further, the sample can be micro-fluidic, allowing x-rays to flow through samples of a different material.

1. An Exemplary Spectrometer System.

FIG. 1 illustrates a block diagram of an exemplary x-ray spectrometer system 200. The spectrometer system 200 of FIG. 1 includes an x-ray source 80, an x-ray optical system 3000 that includes an object 240 to be examined by x-ray transmission, a spectrometer 3700 including detector 290, signal processing electronics 292, and an analysis system 295 having a display 298.

The exemplary x-ray source 80 (e.g., first source) includes a vacuum environment (typically $10^{-6}$ torr or better) commonly maintained by a sealed vacuum chamber 20 or active pumping. Vacuum chamber 20 can be manufactured with sealed electrical leads 21 and 22 that pass from the negative and positive terminals of a high voltage source 10 outside the tube to the various elements inside the vacuum chamber 20. The source 80 can include mounts 30 which secure the vacuum chamber 20 in a housing 50. The housing 50 may include shielding material, such as lead, to prevent x-rays from being radiated by the source 80 in unwanted directions.

Inside vacuum chamber 20, an electron emitter 11 is coupled through lead 21 to the negative terminal of a high voltage source 10, which serves as a cathode and generates a beam of electrons 111, for example by running a current through a filament. Any number of prior art techniques for electron beam generation may be used for the embodiments of the invention disclosed herein. Additional known techniques used for electron beam generation include heating for thermionic emission, Schottky emission (a combination of heating and field emission), emitters including nanostructures such as carbon nanotubes, and by use of ferroelectric materials.

A target 1100 includes a target substrate 1000 and x-ray generating structures 700, which can include one or more x-ray generating materials. Target 1100 is electrically connected to the opposite high voltage lead 22 via target support 32 to be at ground or a positive voltage relative to the electron emitter 11, thus serving as an anode. The electrons 111 accelerate towards the target 1100 and collide with it at high energy, with the energy of the electrons determined by the magnitude of the accelerating voltage. The collision of the electrons 111 into the target 1100 induces several effects, including the radiation of x-rays 888, some of which exit the vacuum chamber 20 and are transmitted through a window 40 designed to be transparent to x-rays.

In some instances, there can also be an electron control mechanism 70 such as an electrostatic lens system or other system of electron optics. Control mechanism 70 can be controlled and coordinated with the electron dose and voltage provided by the electron emitter 11 by a controller 10-1 through an additional lead 27. The electron beam 111 may therefore be scanned, focused, de-focused, or otherwise directed onto target 1100, which can include one or more x-ray generating structures 700 fabricated to be in close thermal contact with a substrate 1000.

Once x-rays 888 exit the x-ray source 80, a portion of the x-rays are collected by optical system 3000. Optical system 3000 can include one or more optical systems 840 having x-ray optical elements with axial symmetry. The elements of the optical system 840 reflect x-rays at grazing angles to focus a portion 887 of the x-rays onto an aperture component 270 having one or more apertures 272. The object 240 to be examined is typically placed in a mount 244 and positioned at the focus or just before the aperture 272. The mount may allow the object 240 to be translated and/or rotated so that different portions of the object 240 are illuminated by the x-ray beams 887, allowing different positions on the object 240 to be illuminated in a systematic scan or from several angles of incidence, with this motion controlled by a controller 246. X-rays propagating along the axis of the optical system that are not collected and focused may be blocked by a beam stop 850.

Once the focused portion of the x-rays 887 converge onto the object 240, the transmitted x-rays 888-T that also pass through the aperture 272 are collected by a spectrometer 3700. The spectrometer 3700 typically includes at least one dispersing x-ray crystal and an x-ray detector 290. The detector 290 will typically be an array detector, positioned to record the intensity of the dispersed x-rays as a function of position. Additional signal processing electronics 292 and analysis system 295 correlate the intensity signals to the corresponding x-ray energy. The analysis system 295 may additionally include a display 298. The detector 290 may also include sensors and electronics that serve as an x-ray spectrometer, analyzing both the number of x-ray fluorescence photons emerging from the object 240 as well as their energy.

Additional embodiments of x-ray sources have been described in U.S. Patent Applications "X-RAY SOURCES USING LINEAR ACCUMULATION" (U.S. patent application Ser. No. 14/490,672, filed Sep. 19, 2014 and now issued as U.S. Pat. No. 9,390,881), "X-RAY SOURCES USING LINEAR ACCUMULATION" (U.S. patent application Ser. No. 14/999,147, filed Apr. 1, 2016, and now issued as U.S. Pat. No. 9,543,109), and "DIVERGING X-RAY SOURCES USING LINEAR ACCUMULATION" (U.S. patent application Ser. No. 15/166,274 filed May 27, 2016), all of which are hereby incorporated by reference in their entirety, along with any provisional applications to which these Patents and co-pending Patent Applications claim benefit.

Any of the target and/or source designs and configurations disclosed in the above referenced Patents and Patent Applications may be considered for use as a component in any or all of the methods or systems disclosed herein. Such variations may include active cooling systems having channels that carry liquid near or into the target to remove heat, mechanisms to rotate the anode to allow different portions to be bombarded by electrons while other recently bombarded portions cool, systems including multiple electron beams that bombard opposite sides of a target to increase x-ray brightness through linear accumulation, and systems that additionally use multiple anodes aligned to create an x-ray beam through linear accumulation from several sources.

The components illustrated in the Figures are exemplary, and the various elements (microstructures, surface layers, cooling channels, etc.) are not intended to be limiting. It should also be noted that the x-ray source used for embodiments of the invention may be a microfocus, nanofocus, or rotating anode source using bombardment of a solid anode target by electrons, but that the target may also include multiple x-ray generating materials, and may additionally contain regions in which the x-ray generating materials are molten or liquid. Furthermore, the x-ray source may be any x-ray source designed to use a liquid metal (such as a gallium liquid metal jet) as the anode.

2. X-ray Source Spectrum.

Figure 2:
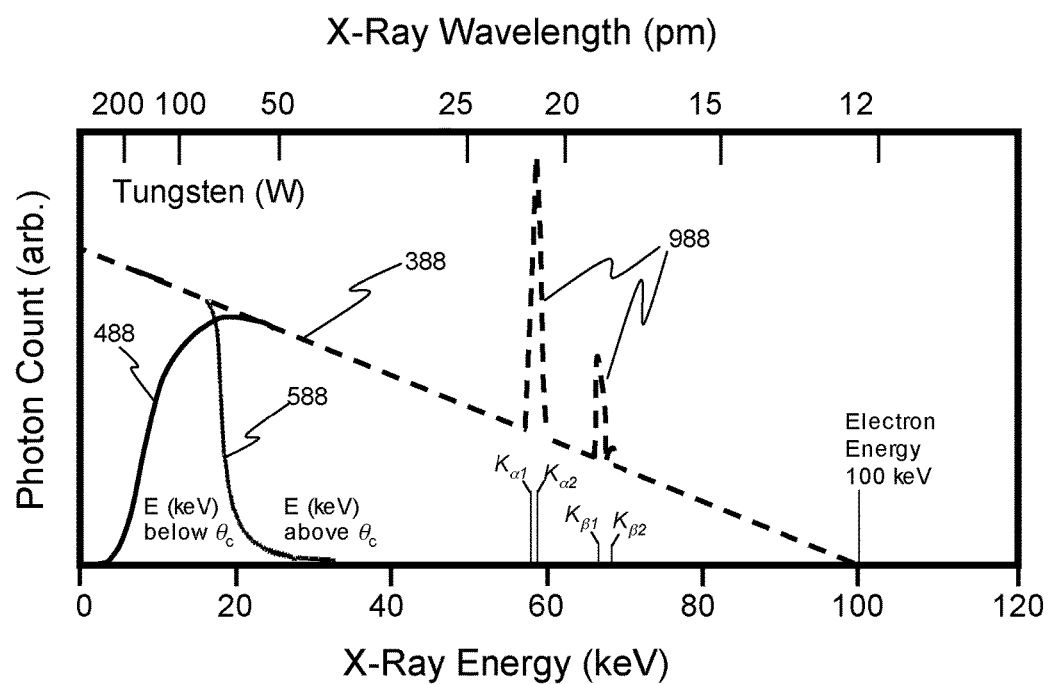
FIG. 2 illustrates an x-ray radiation spectrum.

FIG. 2 illustrates an x-ray radiation spectrum for 100 keV electron excitation with a tungsten (W) target. The broad spectrum x-ray radiation continuum 388, commonly called bremsstrahlung, is larger at lower energy and decreases at energies approaching the excitation energy of 100 keV. Characteristic lines 988 for tungsten are also illustrated.

This exemplary spectrum is modified for use in a spectroscopy system to limit the x-ray bandwidth. As discussed with respect to FIG. 1, the x-ray source 80 will typically have a window 40. This window 40 may attenuate low energy x-rays. Shown in FIG. 2 is a modified energy spectrum 488 for the x-rays that results from using an $SiO_2$ window 100 microns thick. Some laboratory sources either come with a Be window (normally 200-300 um thick) or with a diamond window (normally ~200-300 um thick), which also doubles up as a target substrate in the transmission source type. The system may additionally include a filter, such as a sheet or layer of aluminum, placed near the source or on the window to further attenuate low energy x-rays.

For a spectrometer, broad-spectrum x-rays can be used, and in some instances can be preferred, and characteristic lines 988 may make the task of interpreting the resulting spectra more difficult. It is therefore often advantageous to have the optical system collecting and focusing the x-rays designed to serve as a low-pass filter, severely attenuating any characteristic lines that may be generated and high energy bremsstrahlung background.

The optical system can include one or more x-ray optical elements in which the x-rays illuminates the inner surface of the element at a near-grazing angle (e.g. at angles of a few degrees or smaller). The optics may be coated with a particularly selected material, such that the critical angle of reflection can be exceeded for the higher energy x-rays, and the higher energy x-rays may not be efficiently reflected by the optical surface. As such, the x-ray optical system can have low-pass spectral filter properties such that x-rays above a cut-off energy are reduced as they pass through the optic system. X-rays below the cut-off energy may be focused to a predetermined focal plane.

Also in FIG. 2, a modified energy spectrum 588 that results from using a silver (Ag) coating on the interior of a capillary with a grazing angle of incidence of 3.5 mrad (0.2005 degrees), as calculated using the website henke.1bl.gov/optical_constants/layer2.html.

X-ray energies above 17.4 keV are significantly attenuated, providing 17.4 keV as a "high-energy cutoff" for reflection in this system. This cuts out the strong tungsten characteristic lines at higher energy. When combined with the "high pass" filter provided by the window, the "low-pass" optical system provides a system with a predetermined x-ray "bandwidth".

The "high-energy" cutoff is well defined for a given material with a critical angle, and the attenuation of high energy x-rays prevents spurious signals from being observed at higher harmonics (e.g. twice (2×) the energy) downstream in the spectrometer. However, additional structure in the reflectivity spectrum may be observed at high energy with some materials. For some x-ray reflective optics, the reflectivity may be designed to be below 25% for all energies greater than 1.2 times the cutoff energy. For some x-ray reflective optics, the reflectivity may be designed to be below 10% for all energies greater than 1.2 times the cutoff energy.

3. Structured X-ray Source.

The x-ray bandwidth for a given x-ray source target material and combination of window/filter and x-ray optical system may or may not provide the full range of x-ray energies needed for the measurement of the x-ray absorption spectrum of a given object to be examined. Achieving enough x-ray brightness in the spectral region of interest may be an issue, and therefore, x-ray sources includes targets having x-ray generating materials embedded into a thermally conductive substrate. X-ray source material could include one of several types of sources, including a solid continuous target or a micro-structured target.

Microstructured targets, x-ray generating materials, x-ray target materials, microstructures of different shapes, and microstructures of various materials such as those that may be used in embodiments of the present technology disclosed herein are described in US Patent Application entitled "STRUCTURED TARGETS FOR X-RAY GENERATION" (U.S. patent application 14/465,816, filed Aug. 21, 2014), the disclosure of which is hereby incorporated by reference in its entirety along with any provisional Applications to which said Patent Application claims benefit.

Although the targets may be aligned to radiate x-rays using a zero-degree take-off angle, as discussed above, some embodiments may use near-zero degree take off angles using source configurations as presented in, for example, U.S. patent application Ser. No. 15/166,274, filed May 27, 2016 by the inventors of the present Application and entitled "DIVERGING X-RAY SOURCES USING LINEAR ACCUMULATION," which is hereby incorporated by reference into the present application in its entirety.

Figure 3:
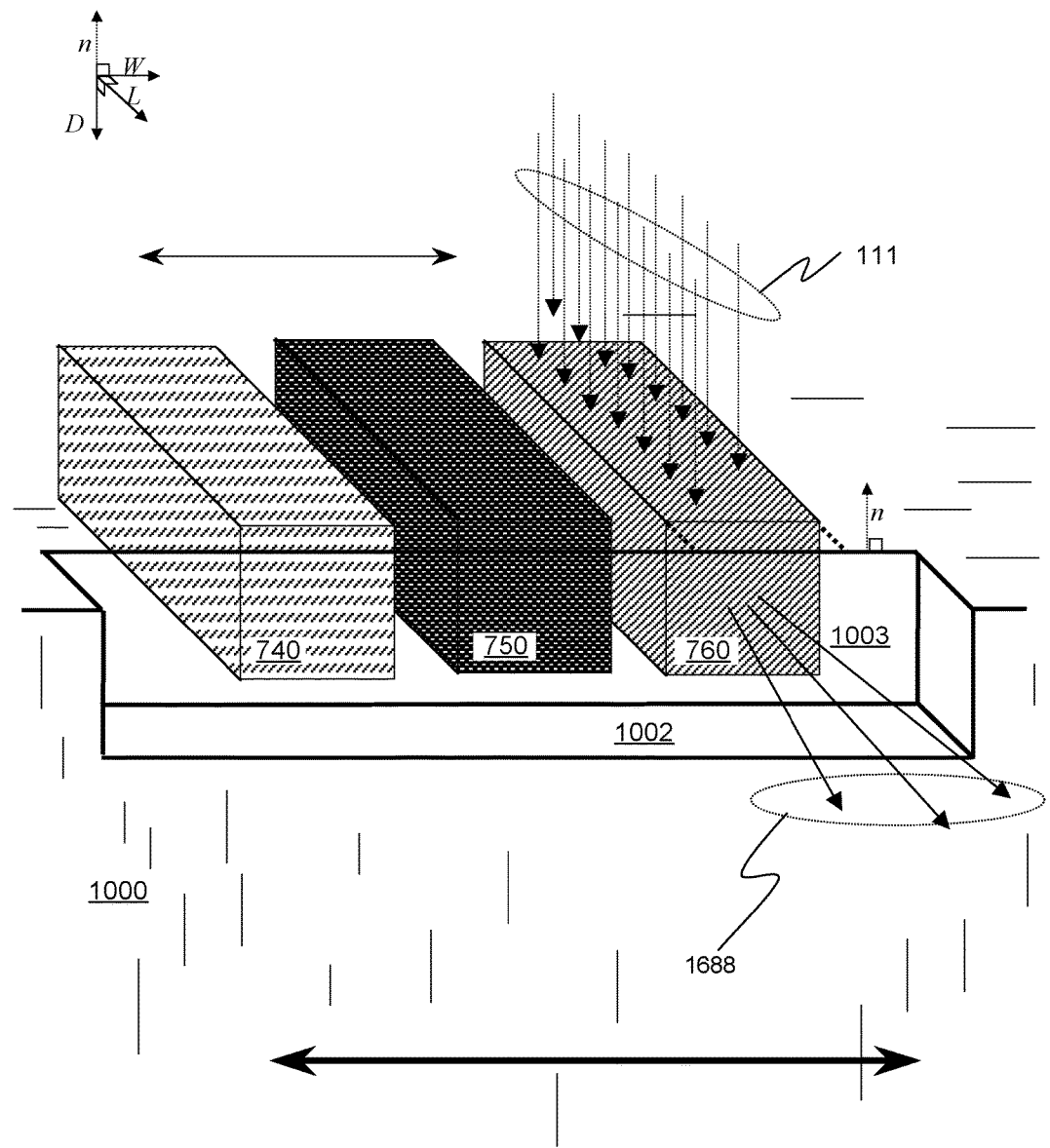
FIG. 3 illustrates a portion of a target comprising three x-ray generating structures, each having a different x-ray generating material, as may be used in some embodiments of the invention.

FIG. 3 illustrates a portion of a target comprising three x-ray generating structures, each having a different x-ray generating material. By translating the target along the width direction so that the electrons 111 now bombard this second set of microstructures, a second set of x-rays 1888 are produced. If the materials of the first set 710 and second set 720 are distinct, the corresponding x-rays 1788 and 1888 generated when selected for bombardment by electrons will also have distinct spectral properties.

Various targets include different x-ray generating materials may be used in various embodiments. As illustrated in FIG. 3, multiple solid structures 740, 750 and 760 of different x-ray generating materials may be used in an anode target as well, with selection between target materials made by translation of the target under the electron beam 111 to select, for example, the third material 760, generating the corresponding x-rays 1688.

Although the physical translation of the target under the electron beam may allow the materials to be "switched" from one to another while producing a beam that remains aligned with a single set of x-ray optics, other embodiments in which the electron beam is simply directed from one set of materials to another may also be used. This may be beneficial in cases where the different x-ray generating materials are aligned with different sets of x-ray optics, with each set of optics tuned to match the radiation spectrum of x-rays for each material. Directing the electron beam from one to the other therefore allows rapid switching between spectral sources.

4. X-ray Optical System.

Once x-rays are generated by a high-brightness x-ray source, a portion of the x-rays can be collected by an optical system to be subsequently collimated and/or focused onto the object to measure the x-ray absorption and transmission.

Optical systems used in embodiments of the invention disclosed herein have been described in detail in the U.S. Patent Application entitled "X-RAY ILLUMINATORS WITH HIGH FLUX AND HIGH FLUX DENSITY" (U.S. patent application Ser. No. 15/431,786, filed Feb. 14, 2017) and its parent Applications (U.S. patent applications Ser. No. 15/269,855, filed Sep. 16, 2016, and now issued as U.S. Pat. No. 9,570,265, and 14/544,191, filed Dec. 5, 2014 and now issued as U.S. Pat. No. 9,449,781), which are all hereby incorporated by reference in their entirety, along with the provisional Applications to which they claim benefit.

Referring to FIG. 1, the generated x-rays will diverge from the x-ray source 80, and after passing from the source through an x-ray transparent window 40, an optical system 3000 includes a set of one or more x-ray optical elements will intersect a portion of the x-rays and redirect their path of propagation.

The optical system 3000 may be a simple, single x-ray reflecting optical element with the topology of a hollow tube, or a more complex set of x-ray optics. This optical system 3000 can be mounted along the axis of brightest illumination so that a portion of the diverging x-rays 888 will reflect off the inner surface of the various optical elements. The curvature of the inner and/or inner and outer surface may take a number of geometric forms, but a very useful set of geometric forms for a number of optical elements are found among the quadric surfaces, and in particular, spheroids, ellipsoids, paraboloids, hyperboloids, elliptic cylinders, circular cylinders, elliptic cones, and circular cones. In some instances, at least a portion of a reflective surface of the reflective x-ray focusing optic is axially symmetric. In some embodiments, the reflective surface may be coated with a material selected for its x-ray reflective properties, including its critical angle. Such materials may include chromium, copper, rhodium, palladium, gold, silver, nickel, iridium, and platinum, among others.

These optical elements will typically be mounted such that a portion of the x-rays experience total external reflection from the inner surface, as was described above. The reflected x-rays from an individual optical element may be focused to a point or a line, or collimated, or configured to produce some other diverging or converging wavefront, but for the embodiments presented here, the optical system produces a converging wavefront of x-rays 887 that comes to a focus at an aperture 272.

By placing an object 240 to be examined where it will be illuminated by the converging x-rays 887, a transmitted diverging x-ray wavefront 888-T is produced on the far side of the aperture 272, and may be subsequently analyzed by the spectrometer.

4.1. Optics Configurations

Optical configurations for use with the present technology can be configured as an ellipse, parabola, paraboloidal, or other shape. FIGS. 4A-5B illustrate exemplary optical reflectors.

Figure 4A:
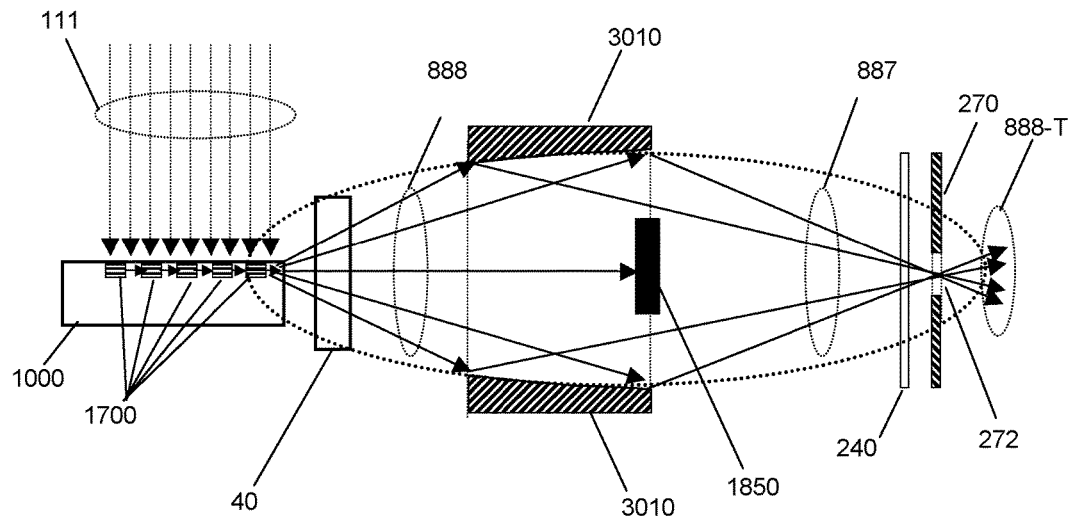
FIG. 4A illustrates a cross section schematic view of an x-ray source and an optical system comprising an ellipsoidal optical element as may be used in some embodiments of the invention.

FIG. 4A illustrates in cross section a possible optical configuration for the optical system using the form of an ellipse. An ellipse has two foci $F_1$ and $F_2$ such that any photons radiating from one of the foci will be reflected and converge onto the other. By configuring the inner surface of a tube-shaped optical element 3010 to have an ellipsoidal surface, and choosing the coating for the reflecting portion of the tube such that the angle of incidence for x-rays within a designated bandwidth emerging from the x-ray source is smaller than the critical angle, total external reflection is achieved. Then, at least a portion of the x-rays generated by an x-ray source placed at one of the foci will be focused to the other focus.

Figure 4B:
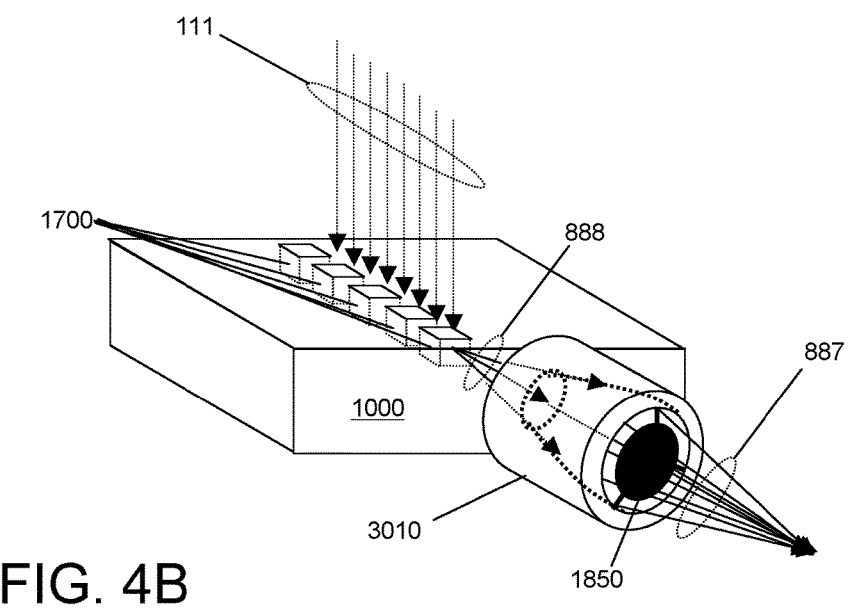
FIG. 4B illustrates a perspective schematic view of a portion of the x-ray source and optical system of FIG. 4A

FIGS. 4A and 4B illustrate a portion of an embodiment of the invention utilizing such an ellipsoidal reflector 3010. An x-ray source includes x-ray generating microstructures 1700 embedded in a substrate 1000 generate x-rays 888 when bombarded by electrons 111 in a vacuum. The diverging x-rays 888 pass through a window 40 and enter the ellipsoidal optical element 3010. A portion of the x-rays experience total external reflection from the inner elliptical surface of a tube-like optical element 3010, and become focused x-rays 887 that converge onto an aperture 272 in an aperture component 270 after passing through the object 240 to be examined. In some embodiments, the on-axis x-rays may be blocked with a beam stop 1850. In some embodiments, as illustrated in FIG. 4A and the corresponding perspective view of FIG. 4B, the on-axis x-rays may be blocked with a beam stop 1850.

Figure 5A:
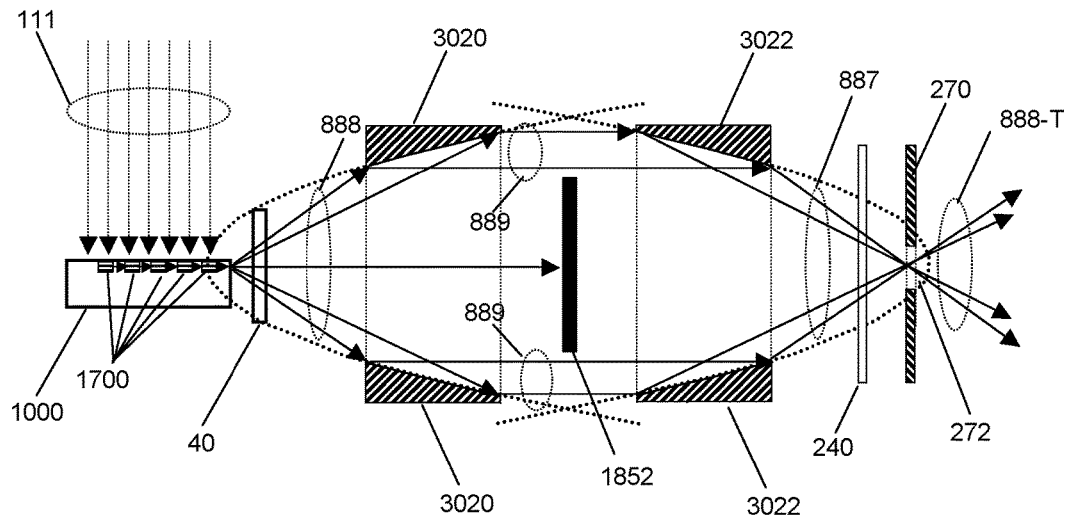
FIG. 5A illustrates a cross section schematic view of an x-ray source and an optical system comprising a pair of paraboloidal optical elements as may be used in some embodiments of the invention.
Figure 5B:
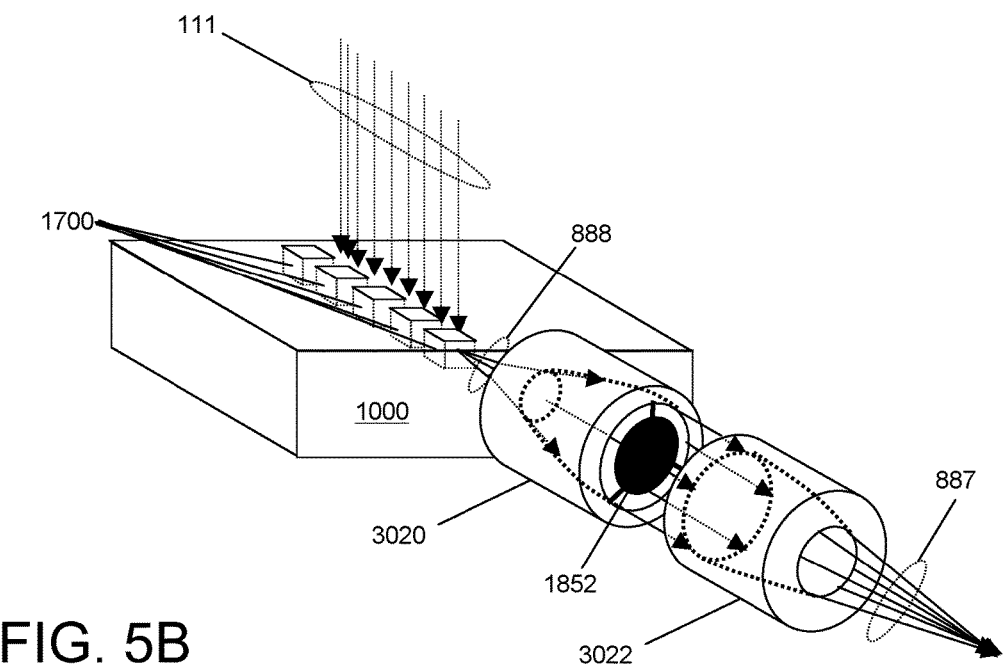
FIG. 5B illustrates a perspective schematic view of a portion of the x-ray source and optical system of FIG. 5A

FIGS. 5A and 5B illustrate a portion of an embodiment of the invention utilizing a paraboloidal reflector 3020. An x-ray source includes x-ray generating microstructures 1700 embedded in a substrate 1000 generate x-rays 888 by linear accumulation when bombarded by electrons 111 in a vacuum. A parabola has single focus $F_p$ such that any photons radiated from the point of focus will be reflected to form a parallel (collimated) beam. The diverging x-rays 888 pass through a window 40 and enter the first paraboloidal optical element 3020. A portion of the x-rays experience total external reflection from the inner paraboloidal surface of the tube-like optical element 3020, and become collimated x-rays 889.

Once collimated, a second optical element 3022 with a tube-shaped topology and paraboloidal inner surface, as shown in FIGS. 5A and 5B, may be aligned with the optical axis of the first optical element 3020 so that the collimated x-rays 889 are incident on the inner surface of the second optical element 3022 at angles smaller than the critical angle for the surface. The reflected x-rays then become focused x-rays 887 that converge onto an aperture 272 after passing through the object 240 to be examined.

Although the illustration shows a second paraboloidal optical element 3022 of the same size and shape as the initial paraboloidal optical element 3020, these need not be the same dimensions, but may have paraboloid surfaces with different curvature and relative focus positions.

In some embodiments, as illustrated in FIG. 5A and the corresponding perspective view of FIG. 5B, the on-axis x-rays may be blocked with a beam stop 1852. Although shown positioned between the two paraboloidal optical elements, the beam stop may be at the entrance to the first optical element 3020, or at the exit of the second optical element 3022 as well.

4.3. Other X-ray Optics.

Other x-ray optical systems, such as Wolter Type I optics, cone shaped capillary optics, Kirkpatrick-Baez optics, etc. may be used as components of the optical system. Systems including filters and additional beam stops, etc. may also be used.

The optical elements described above may be fabricated of any number of optical materials, including glass, silica, quartz, BK7, silicon (Si), Ultra-low expansion glass (ULE™), Zerodur™ or other materials.

The reflective coatings used for the various optical elements used in embodiments of the invention as described above may be of a single elemental material, to take advantage of the total external reflection for angles of incidence smaller than the critical angle, and preferably may be of higher mass density material (greater than 2.5 g/cm$^3$) at least 25 nm thick. Materials such as gold (Au), silver (Ag), platinum (Pt), etc. may be used as single-material coatings for these optical elements.

The reflective coatings may also be multilayer coatings, with alternating periodic layers of two or more materials, that provide constructive interference in reflection for certain x-ray wavelengths. The reflection efficiency depends on the wavelength and angle of incidence of the x-rays as well as the thickness of the alternating layers and number of layers, so this has limited use as a broadband reflector, but may be used if specific wavelengths are desired. A multilayer could also be depth graded and so the energy bandwidth could be "reasonably large," such as for example 20-25% bandwidth has already been demonstrated for hard x-rays.

Combinations that may be used for multilayer reflectors may be tungsten/carbon (W/C), tungsten/silicon (W/Si), tungsten/tungsten silicide (W/WSi$_2$), molybdenum/silicon (Mo/Si), nickel/carbon (Ni/C), chromium/scandium (Cr/Sc), lanthanum/boron carbide (La/B$_4$C), tungsten/boron carbide (W/B$_4$C), and tantalum/silicon (Ta/Si), nickel/boron carbide (Ni//B$_4$C), and aluminum/alumina (Al/Al$_2$O$_3$), among others. The surface may also be a compound coating that includes an alloy or mixture of several materials.

Other optical elements, such as Fresnel Zone Plates, cylindrical Wolter optics, Wolter Type II optics, Kirkpatrick-Baez mirrors, Wolter Type III optics, Montel optics, diffraction gratings, crystal mirrors using Bragg diffraction, hole-array lenses, multi-prism or "alligator" lenses, rolled x-ray prism lenses, "lobster eye" optics, micro channel plate optics, or other x-ray optical elements may be used or combined with those already described to form compound optical systems for embodiments of the invention that direct x-rays in specific ways that will be known to those skilled in the art.

5.0 Basic Spectrometer.

Figure 6:
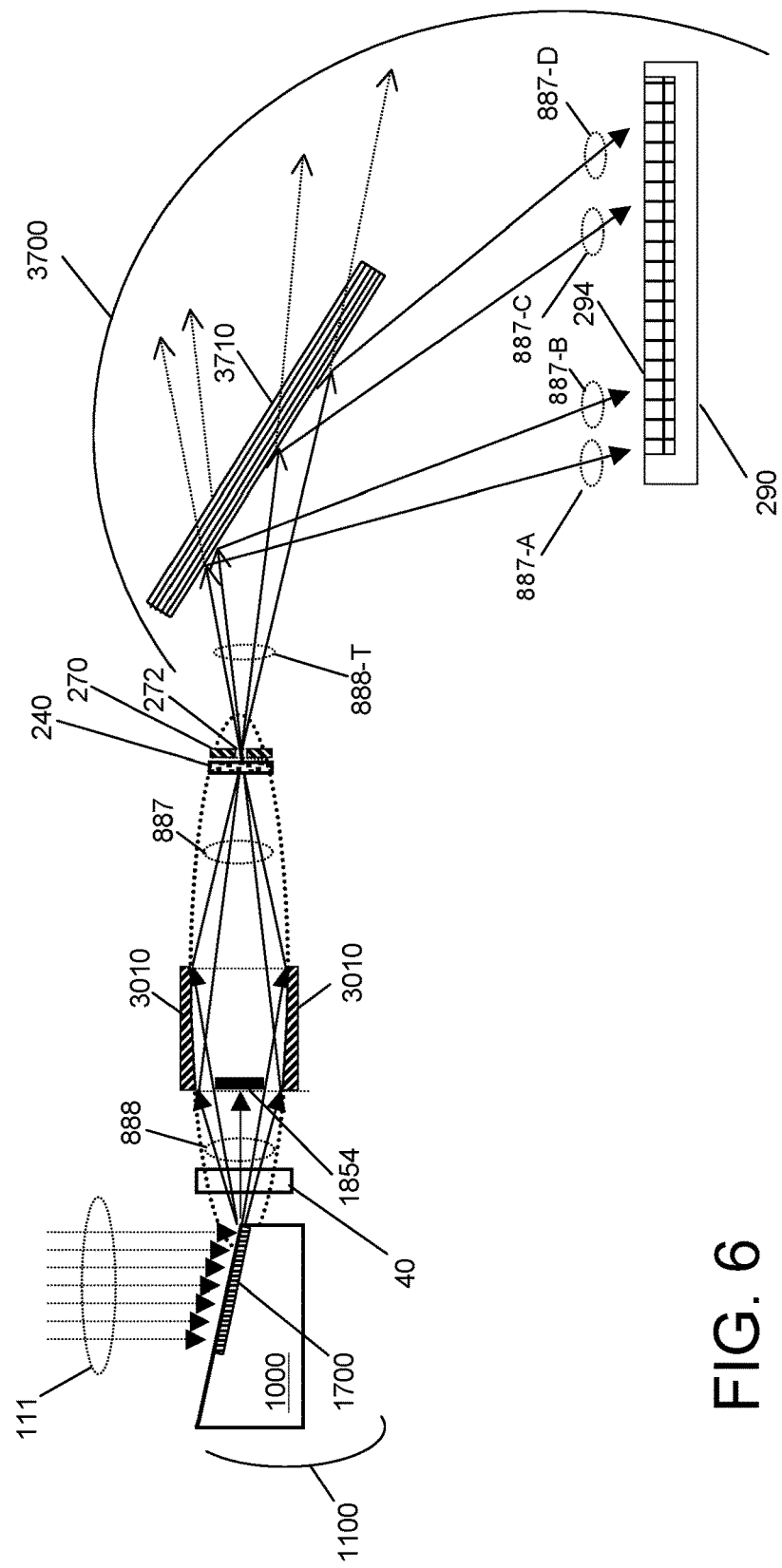
FIG. 6 illustrates a cross section schematic view of a spectrometer system using a single crystal analyzer according to the invention.
Figure 7:
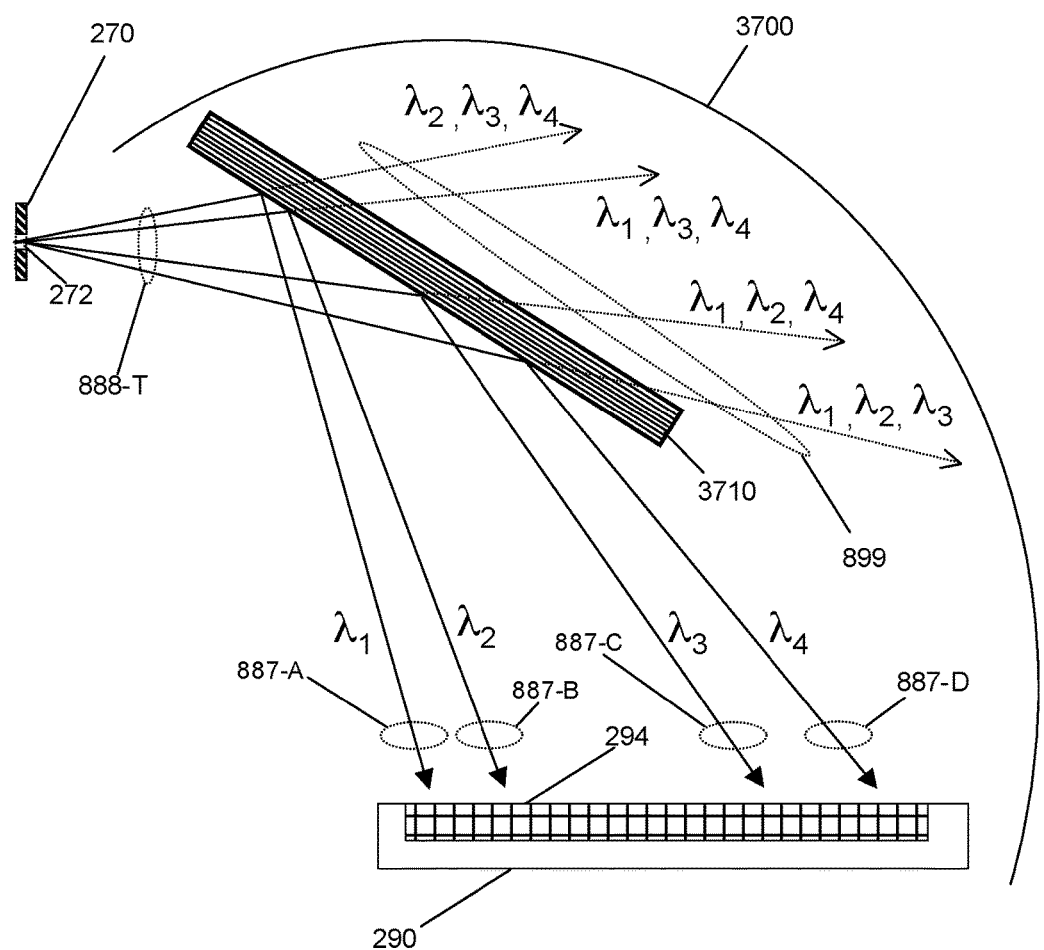
FIG. 7 illustrates a cross section schematic view of the spectrometer portion of the system illustrated in FIG. 11.

FIGS. 6-9 illustrate schematic cross-section views and a perspective view the elements of a spectrometer system that may be used in some embodiments of the invention. Turning to FIG. 6, the x-ray target 1100 includes a substrate 1000 and x-ray generating material 1700 bombarded by electrons 111 in a vacuum. As drawn, the x-rays 888 emerge at a non-zero take-off angle relative to the surface, but other alignments using a zero-degree take-off angle may be used as well.

The x-rays 888 that diverge from the x-ray source pass through the window 40 in the vacuum chamber, and are collected by an optical system. In the example of FIGS. 6-9, the optical system includes a single ellipsoidal capillary optic 3010 and a beam stop 1854. This single optic 3010 has an inner surface that reflects x-rays at near-grazing angles and focuses them onto the aperture 272 in the aperture component 270. An object 240 to be examined is positioned before the aperture component 270, and the x-rays passing through the aperture 272 are those that have been transmitted through the object 240.

The aperture 272 will typically be a small hole of a diameter comparable to the size of the focused spot produced by the x-ray optical system. Aperture diameters of 5 to 25 microns may be typical in some embodiments of the invention. In some embodiments of the invention, the aperture may include a slit, in some instances generally oriented horizontally. The size of the aperture will generally be designed to correspond to the expected size and dimensions of the focused x-ray beam. The aperture component itself may include a piece of metal (e.g. molybdenum or platinum) having a thickness shorter than the depth of focus for the optical system (e.g. on the order of 20 microns thick).

On the far side of the aperture component 270, the x-rays emerge from the focus and are again diverging x-rays 888-T. The geometry will generally be an annulus of x-rays, as defined by the exemplary x-ray optic 3010. As shown, the aperture 272 serves as the point of origin for the x-rays entering the spectrometer 3700. Additional aperture(s) may also be used within the spectrometer to further block scattered x-rays.

In the spectrometer, the cone of x-rays 888-T will fall onto the surface of a diffracting crystal analyzer 3710, which will diffract x-rays of different wavelengths $\lambda_1$, $\lambda_2$, $\lambda_3$ $\lambda_4$, etc. (shown as ray bundles 887-A, 887-B, 887-C, and 887-D etc., respectively) to different points on an array detector 290. As shown in FIG. 5 and, in more detail in FIG. 6, the crystal analyzer will act as a Bragg diffraction element, reflecting the x-rays if the correct conditions of wavelength and angle of incidence are met. X-rays that are not diffracted 899 are typically transmitted through the crystal analyzer, and may be absorbed by a beam stop (not shown) or by the crystal, or by the crystal's mount.

In some instances, multiple crystals can be used in the x-ray spectrometer. When more than one crystal is used, each of the crystals may be selected based on monochromaticity requirements.

The crystal analyzer 3700 may be positioned ~250 mm away from the aperture 272, and will typically have a width of about 1 cm. and a length smaller than 5 cm., but other dimensions may be used. The crystal analyzer 3700 may include a single planar Bragg crystal, but in practice, the crystal analyzer may be a thin crystal curved in the sagittal direction. This allows the x-rays diverging in the directions perpendicular to the direction of propagation to be collected and focused onto the detector 290, while allowing the x-rays to be diffracted by wavelength along the direction of propagation. For some embodiments, a bending radius between 50 and 200 mm may be used. Such configurations are sometimes called a von Hamos Spectrometer.

Curved crystal analyzers such as those made from thin wafers of single crystal silicon with (111) and (220) planes parallel to the surface may be used in some embodiments of the invention. Single crystal silicon analyzers may be grown onto a curved substrate or bent and glued to a similarly shaped substrate.

In some instances, crystal analyzers can include graphite, highly oriented pyrolytic graphite (HOPG), or highly annealed pyrolytic graphite (HAPG). These embodiments may be produced by growing a graphite layer (e.g., 5 and 200 microns thick) onto a curved substrate.

Figure 8A:
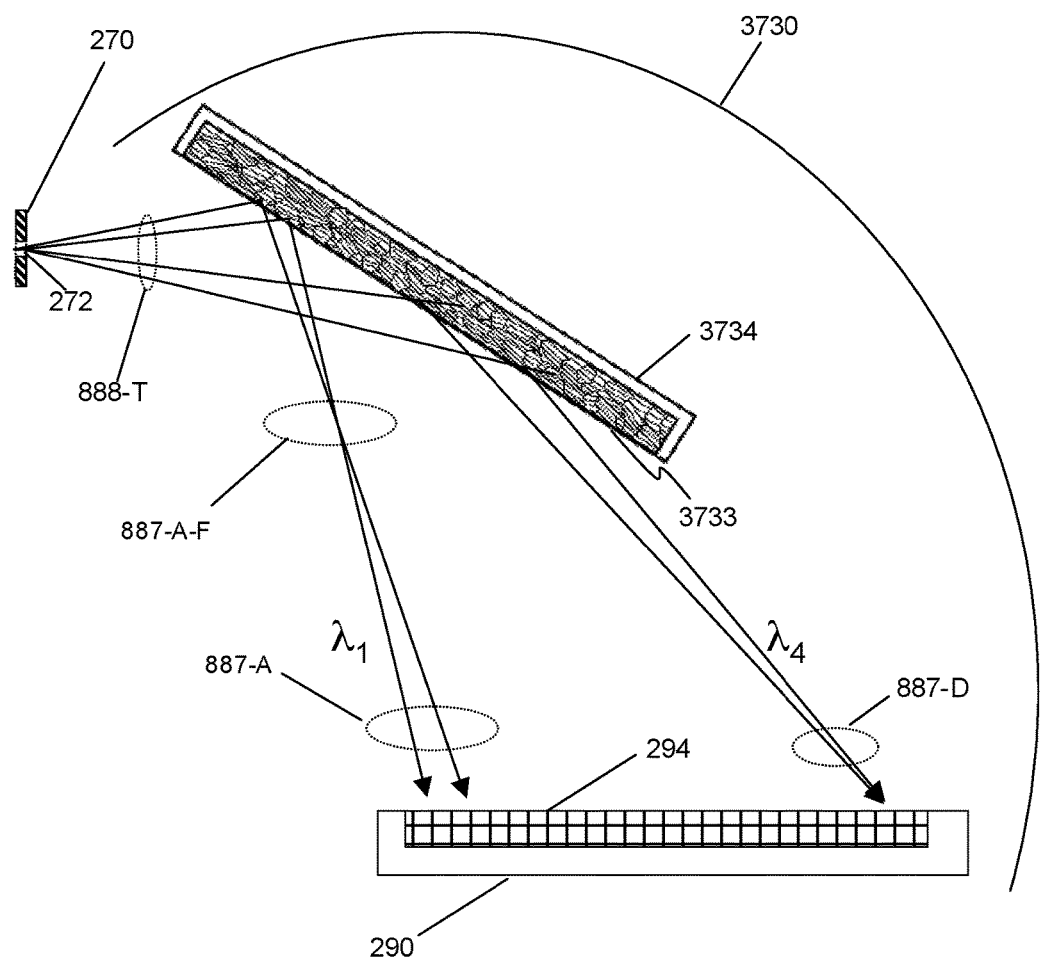
FIG. 8A illustrates a cross section schematic view of the spectrometer portion of a system similar to that illustrated in FIG. 11, but using a mosaic crystal.
Figure 8B:
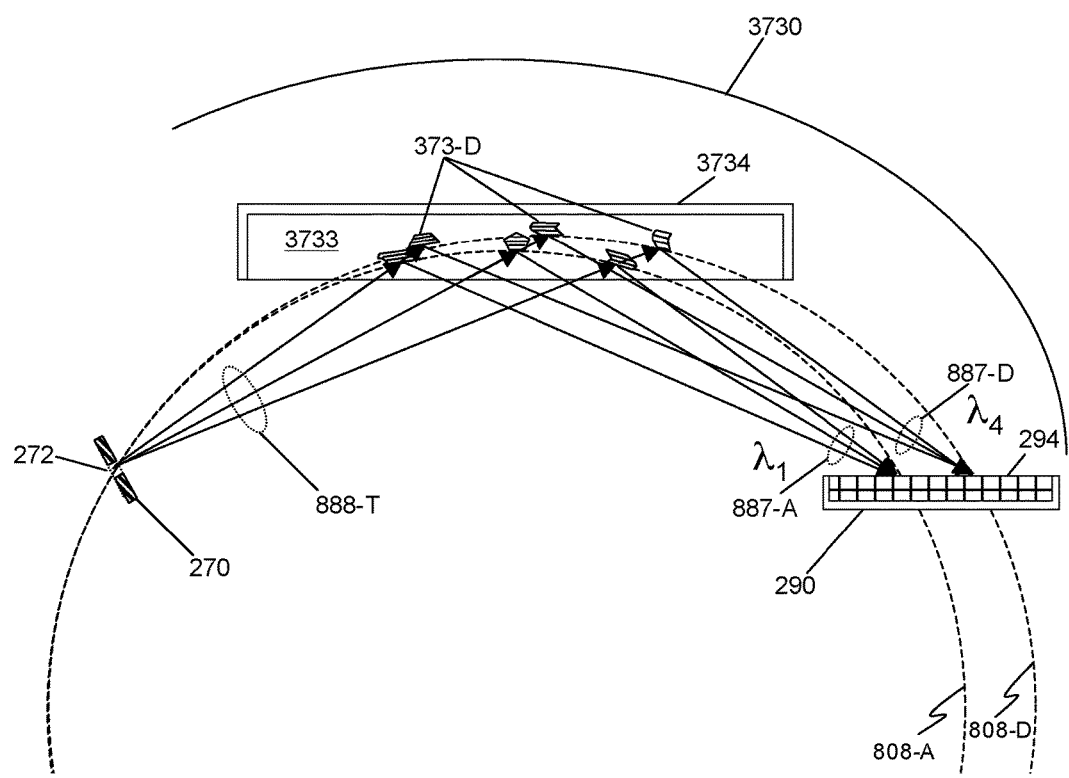
FIG. 8B illustrates a schematic view of a spectrometer such as that illustrated in FIG. 13B, additionally arranged to show the related Rowland Circles.

FIGS. 8A and 8B illustrate a spectrometer 3730 using a crystal analyzer in the form of a mosaic crystal 3733. In the mosaic crystal 3733, the crystal analyzer includes an ensemble of micro-crystals at varied angles throughout the material, each as small as a few hundred nanometers or as large as several microns, held with a backing 3734, typically made of metal. Transmitted x-rays that were not diffracted by the micro-crystal at the surface may still be diffracted from another micro-crystal positioned deeper within the mosaic.

Although the entire spectrum of x-rays transmitted through the object 240 will be present at all points of the transmitted annulus of x-rays 888-T, dispersion is achieved because the diverging cone has a variety of angles of incidence on the crystal analyzer, and therefore for at least some angle of incidence, x-rays of a particular energy within the designated x-ray bandwidth may be reflected. However, all other wavelengths at the same angle of incidence will not be diffracted, and will be partially or completely absorbed by the crystal analyzer shown as transmitted x-rays 899 in FIGS. 5 and 6).

FIG. 8B illustrates the relationship for which additional collection of x-rays may occur. The origin (the aperture in this case), the diffracting crystal, and the point of convergence at the detector all fall along the Rowland Circles 808-A and 808-D for the corresponding wavelengths. Although other micro-crystals are present in the mosaic crystal, only those that lie along the Rowland Circle and have the correct orientation will diffract x-rays to converge to the same position at the detector 290. X-rays of varying wavelengths distributed throughout the diverging beam 888-T have a better chance of encountering a properly positioned and oriented micro-crystal, increasing the number of x-rays directed towards the detector. Use of mosaic crystals can collect as much as 30 times the amount of x-rays that a single crystal diffraction element can produce.

FIG. 8B includes the elements of FIG. 8A, but additionally shows the Rowland Circles 808-A and 808-D for the two x-ray wavelengths, and also only illustrates representative micro-crystals on the mosaic crystal contributing to the diffraction for the two wavelengths. Although micro-crystals with "random" orientations are illustrated in FIG. 8A to dramatically illustrate the mosaic non-uniformity, most mosaic crystals will be more closely aligned with the Bragg angles at the angles of incidence for which they are designed.

Figure 9:
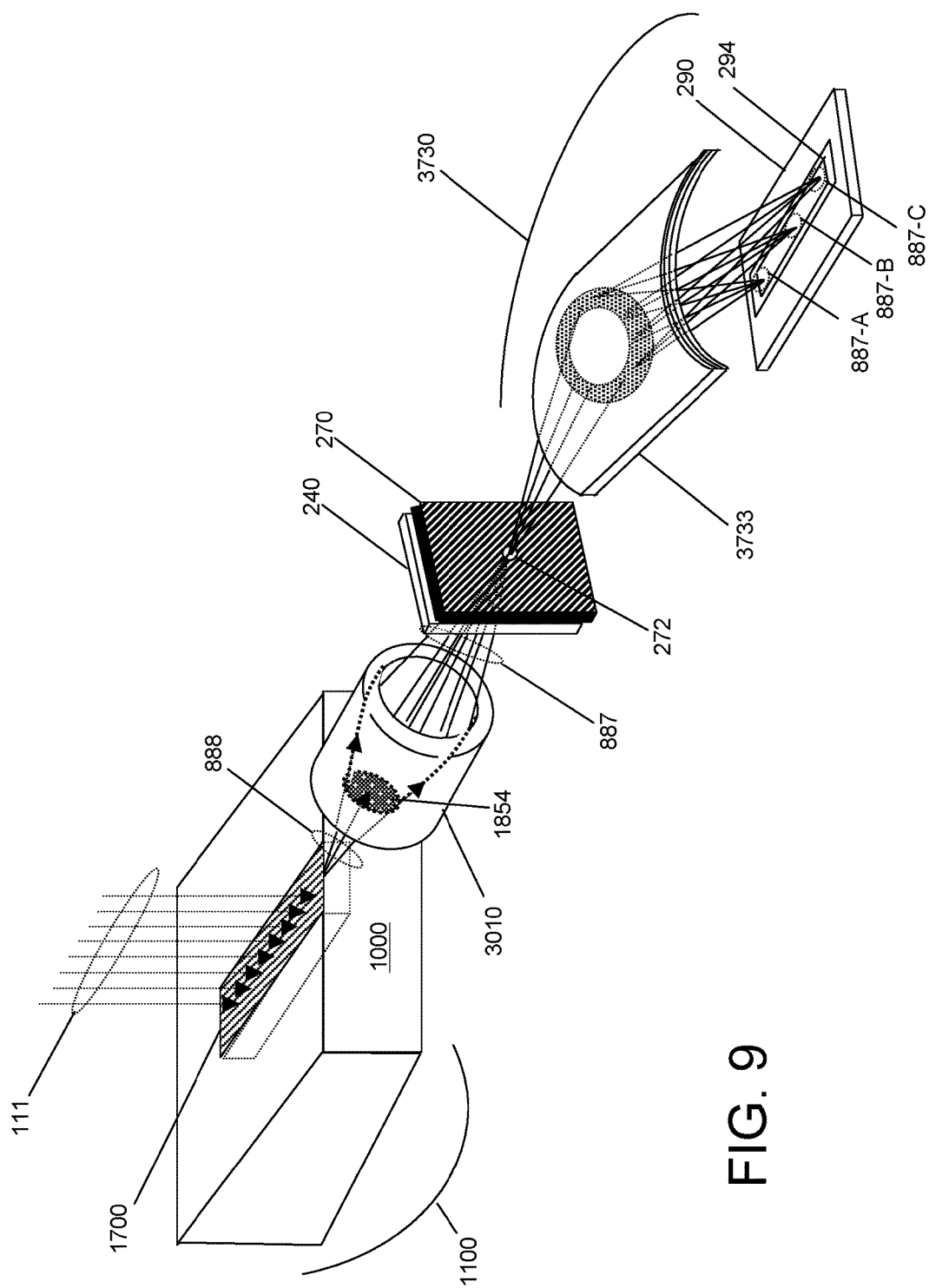
FIG. 9 illustrates a perspective schematic view of a spectrometer system as may be used in some embodiments of the invention.

FIG. 9 illustrates a schematic perspective view of a system using a curved crystal analyzer having a mosaic crystal that distributes the spectrum along one axis, while focusing x-rays in the other (sagittal) axis. As noted before, it should be clear that the drawings presented here are not illustrated to scale, but have been created to better point out how the invention is to be made and used.

For more on crystal or multilayer reflectors, see James H. Underwood, "Multilayers and Crystals", Section 4.1 of the X-ray Data Booklet, which may be downloaded at: xdb.1bl.gov/Section4/Sec_4-1.pdf, and which is hereby incorporated by reference.

5.2. Detectors.

The detector 290 typically includes a 2-D pixel array 294, in which one axis is significantly longer than the other. A 2048×256 pixel array may be typically used, although a detector with at least 128 pixels along the long axis (the dispersive direction) may be preferred. For some configurations where the beam cross sections are smaller and the distances are shorter, fewer pixels may be used. Also, if a portion of the beam is to be blocked, fewer pixels may be used. The long axis will be aligned along the direction of x-ray propagation, and the dispersion of x-rays by wavelength will occur along that axis. The short axis will be aligned with the sagittal direction. The diffracted x-rays may not form a perfect spot, and so detection using multiple pixels may provide a higher collection efficiency.

The detector may be any one of a number of x-ray array detectors, such as a CCD array, a CMOS or S-CMOS detector, a flat panel sensor, or any one or more position sensitive x-ray array detectors known in the art that converts x-ray intensity to an electronic signal, including 1-D line and 2-D array detectors. Such examples of position-sensitive detectors include linear detectors, position-sensitive array detectors, pin diodes, proportional counters, spectrometers, photodiode detectors, scintillator-type and gas-filled array detectors, etc.

Energy resolving pixel array detectors may also be used. In these detectors, each pixel also provides information on the energy of x-rays detected, and may be especially useful when the object produces significant fluorescence. Also known as energy resolving x-ray spectrometer, such a detector uses a semiconductor device to measure the energy of the detected x-ray photons. The silicon PIN photodiode (Si-PIN) is a simple and low cost class of EDS spectrometer that typically has the lowest performance in terms of energy resolution. Energy resolving pixel array spectrometers are available and may be used in some embodiments of the invention.

Another type of detector, known as a pixel array microcalorimeter spectrometer, uses typically a superconductor circuit to measure change of the electric response from absorption of an x-ray photon.

In some instances, the spectrometer may include a mechanism, such as a shielding component, that prevents undesired x-rays from being detected. For example, at least one x-ray shielding component can be implemented that prevents x-rays not-dispersed by the wavelength dispersive component from arriving at the detector.

Additional configurations may involve additional filters (e.g. thin foils containing the appropriate element(s)) along the beam path before the detector to preferentially attenuate some unwanted x-rays from arriving at the spectrometer, reducing the background due to the detection of the x-rays scattered from the object or reduce total x-ray flux entering the spectrometer to avoid saturation. Multiple spectrometers of the same type or combination of two or more types can be used simultaneously or interchangeable to utilize their respective strength individually or collectively.

Other detector geometries and arrangements may be known to those skilled in the art. For more on x-ray detectors, see Albert C. Thompson, "X-Ray Detectors", Section 4.5 of the X-ray Data Booklet, which may be downloaded at: xdb.1bl.gov/Section4/Sec_4-5.pdf which is also hereby incorporated by reference.

5.3. Options and Versatility.

As discussed above, a single x-ray generating material combined with a selected coating for an x-ray optic may provide a limited bandwidth for an x-ray optical system that avoids unwanted characteristic lines and provides a particular region of an absorption spectrum for an object to be investigated. However, any given x-ray generating material with any given optical coating will generally not provide the full spectral range needed to characterize an object in transmission.

Figure 10:
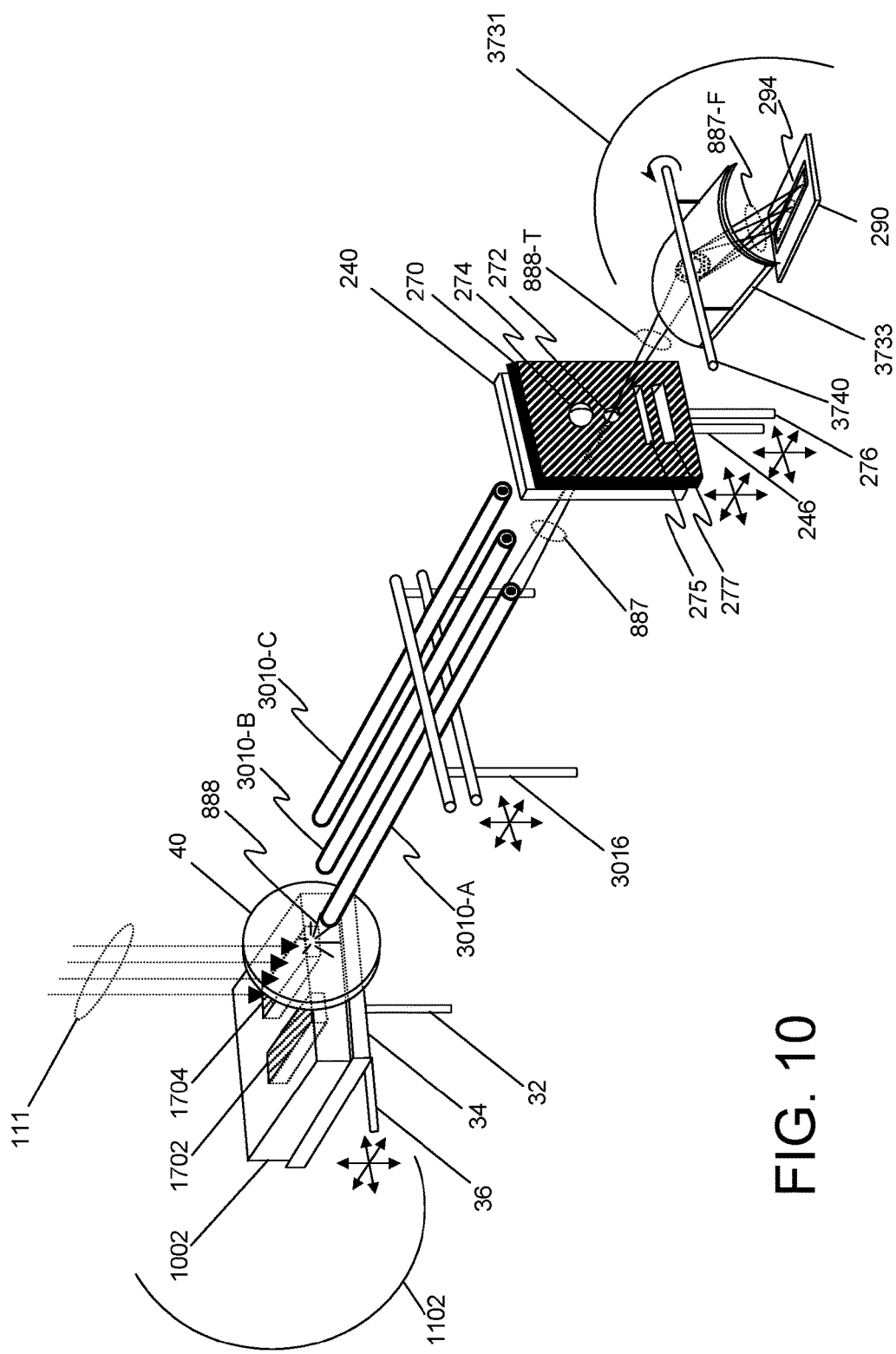
FIG. 10 illustrates a perspective schematic view of a spectrometer system having multiple options for x-ray source, optical system, aperture, and crystal analyzer position as may be used in some embodiments of the invention.

FIG. 10 provides a schematic illustration of a spectrometer system having a diversity of options built into the system. The target 1102 includes a substrate 1002 and two (or more) different types of x-ray generating materials 1702 and 1704. The mount 34 upon which the target is secured not only connects to the electrical lead 32, but also has a controller 36 that allows physical motion in a lateral direction for the selection of the material to be bombarded by electrons 111.

The system of FIG. 10 also has three different optical systems 3010-A, 3010-B and 3010-C supported in a mount 3016 that allows the set of optical systems to be moved laterally to allow alignment of any of the optical systems (which may use different material coatings and filters inside to allow different x-ray bandwidths) with any of the x-ray generating targets 1702, 1704 etc. As illustrated, the right-most x-ray generating material 1704 is being bombarded by electrons, and the left most optical system 3010-A is positioned to collect the x-rays transmitted through the window 40.

As before, the converging x-rays 887 emerging from the optical system are focused onto an aperture 272 in an aperture component 270, and also pass through the object 240 to be investigated. The resulting x-rays diverging from the aperture 272 become the "virtual origin" for the x-rays diffracted by the spectrometer 3700.

However, the aperture component 270 may have multiple openings, such as circular apertures 272 and 274 having different sizes, or slits 275 and 277 of different sizes.

As before, the spectrometer 3731 includes a mosaic crystal analyzer 3733 that disperses the x-rays onto the x-ray sensor 294 of the detector 290. However, in case the wavelength range is insufficient to span the entire spectrum in a single shot, this spectrometer 3731 also includes a mount 3740 that allows the crystal analyzer 3710, an x-ray wavelength dispersive element, to rotate about an axis perpendicular to the direction of x-ray propagation. This allows a larger range of x-ray dispersion to be measured using a single detector.

Such a multi-source/multi optic system may be used to collect x-ray spectra in a sequence of bands. For example, a first measurement may be taken using a source/optic combination to provide an x-ray spectrum between 4 and 5 keV; the next a different combination to provide a spectrum between 5 and 6 keV; and the next a third combination to provide a spectrum between 6 and 7 keV, etc. Rotation of the crystal about the axis may expand the range of energies collected from the same source/optic combination.

In other variations, optical systems with a variety of beam stops may be used. Beam stops may be positioned at the entrance to the optical system, at the exit of the optical elements of the optical system, or in between elements of the optical system. In some embodiments with a single condenser optic, there may be a stop on both the entrance side and the exit side of the condenser optic, with the exit-side stop being ~⅔ the size of the entrance stop. These stops will both block the through-beam, and in addition, the exit stop will also block a good portion of any scattered x-rays from the condenser optic. This provides for a cleanly reflected x-ray beam.

In other variations, a number of shielding elements may be used to block or reduce unwanted x-rays from being detected. Scattering and x-ray fluorescence may occur every time x-rays encounter a component of the system. Likewise, x-rays not diffracted by the crystal analyzer will be transmitted through the analyzer, and may create additional scattered and/or fluorescence x-rays unless a suitable beam absorbing element is positioned behind the analyzer. Although these unwanted x-rays will not propagate along the principle beam-path of the system in the way that the focused x-rays propagate, they may still find their way through the system and onto a detector element unless additional shielding is installed.

In other variations, the entire system (and not just the x-ray source) may be enclosed in a vacuum chamber, removing the need for the window 40 be present to maintain the vacuum around the x-ray source. Likewise, the optical system and spectrometer may be flushed with helium gas, to reduce scattering in the system.

5.4. X-ray Emission Spectroscopy (XES).

Figure 11:
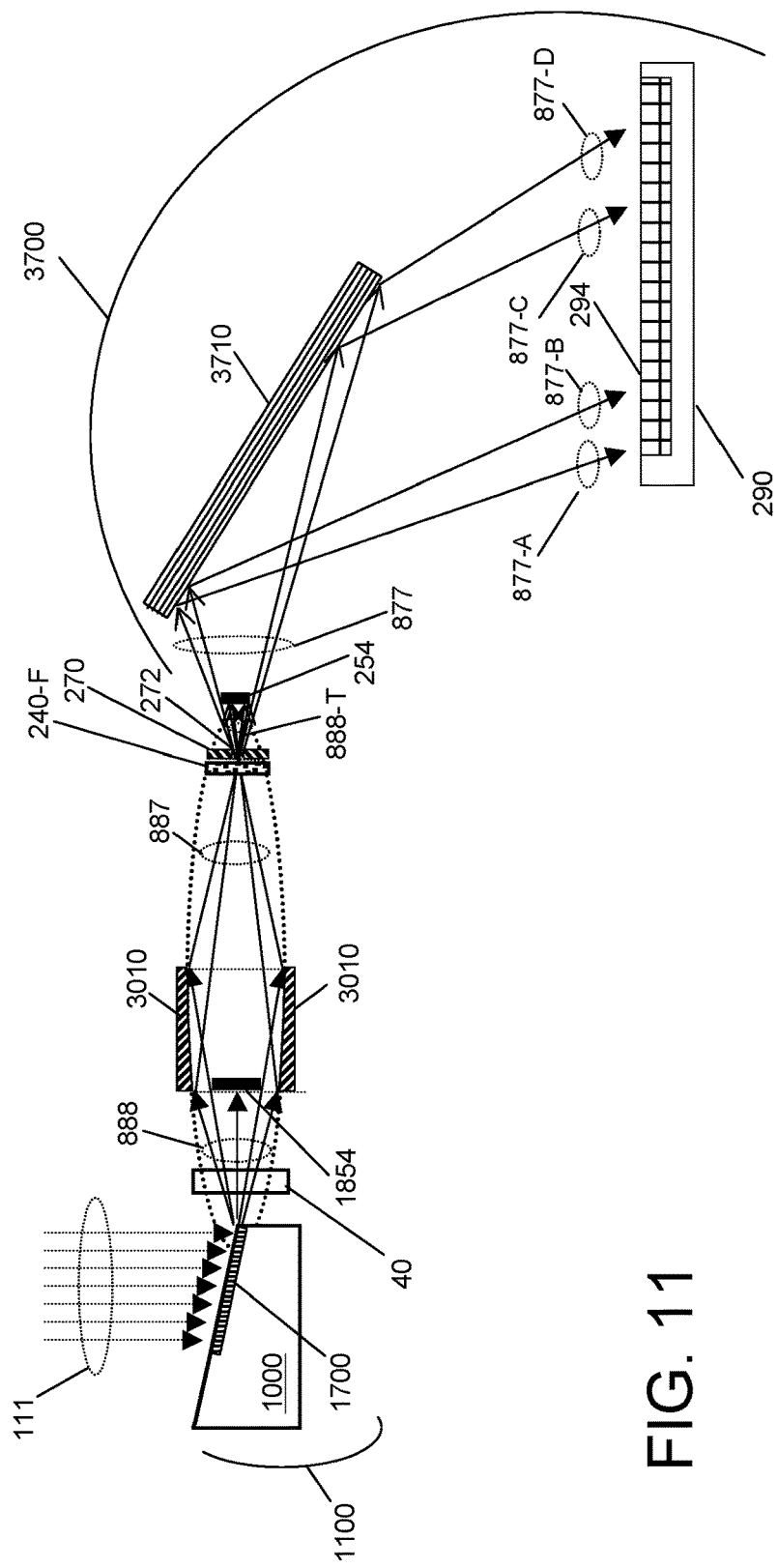
FIG. 11 illustrates a cross section schematic view of a spectrometer system using a single crystal analyzer according to the invention.

Another embodiment adapted to detect the spectrum of x-ray fluorescence for use in x-ray emission spectroscopy (XES) is shown in FIG. 11. The embodiment of FIG. 11 is similar to the configuration illustrated in FIG. 6, except the object 240-F emits x-ray fluorescence 877. This fluorescence will generally be emitted in all directions from the object 240-F. Therefore, to block the x-rays 888-T directly transmitted through the object 240-F, a beam stop 254 is positioned after the aperture component 270, and only the x-ray fluorescence 877 emerging from the object 240-F around the beam stop 254 propagates onward to the crystal analyzer 3710. The crystal analyzer 3710 then disperses the fluorescence according to wavelength, with x-rays 877-A, 877-B, 877-C, 877-D, etc. of different wavelengths directed to different positions on the detector sensor 294.

6.0 Methods of Spectroscopic Data Gathering.

Figure 12A:
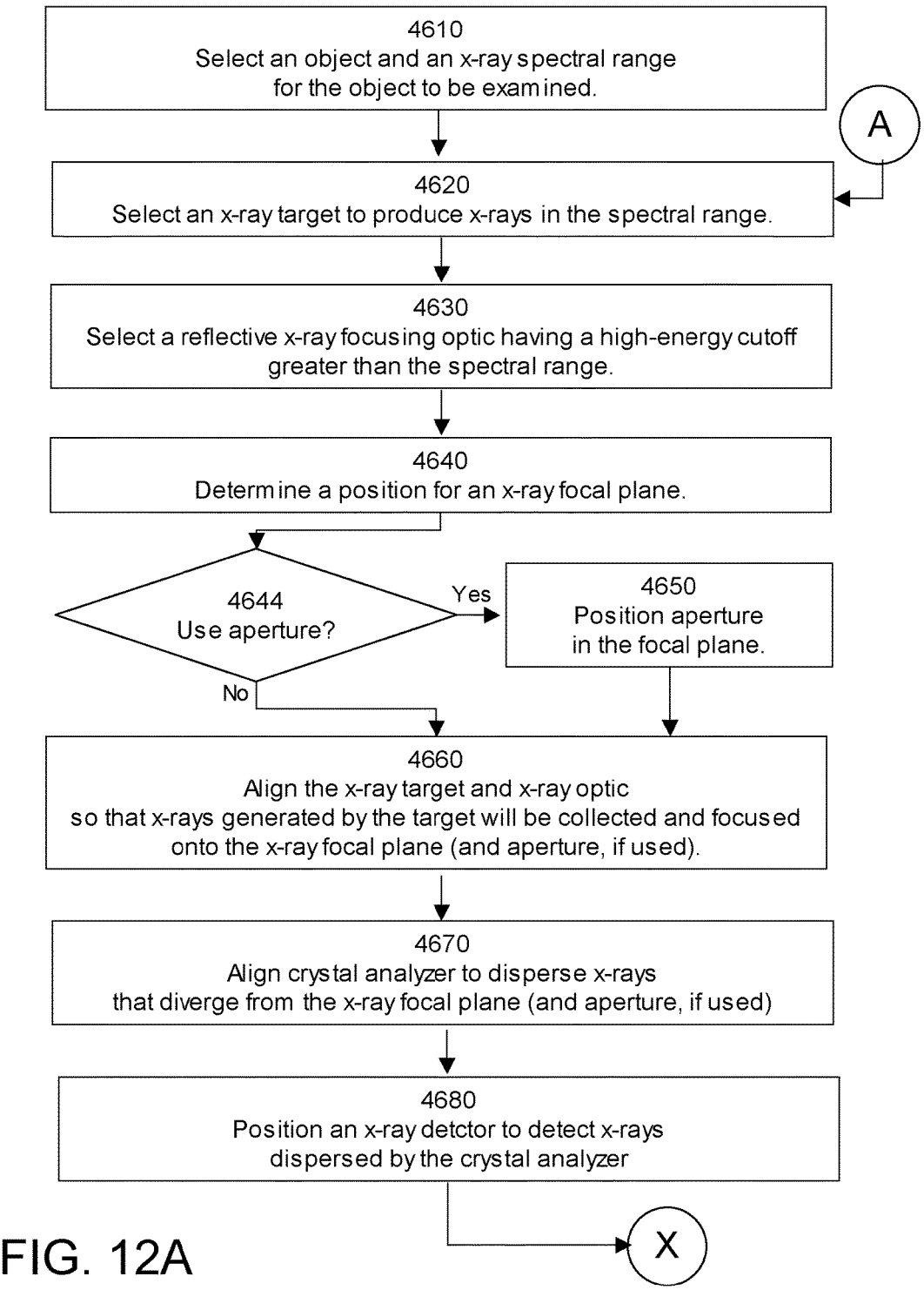
FIG. 12A presents a portion of the steps of a method for collecting spectroscopy data according to an embodiment of the invention.
Figure 12B:
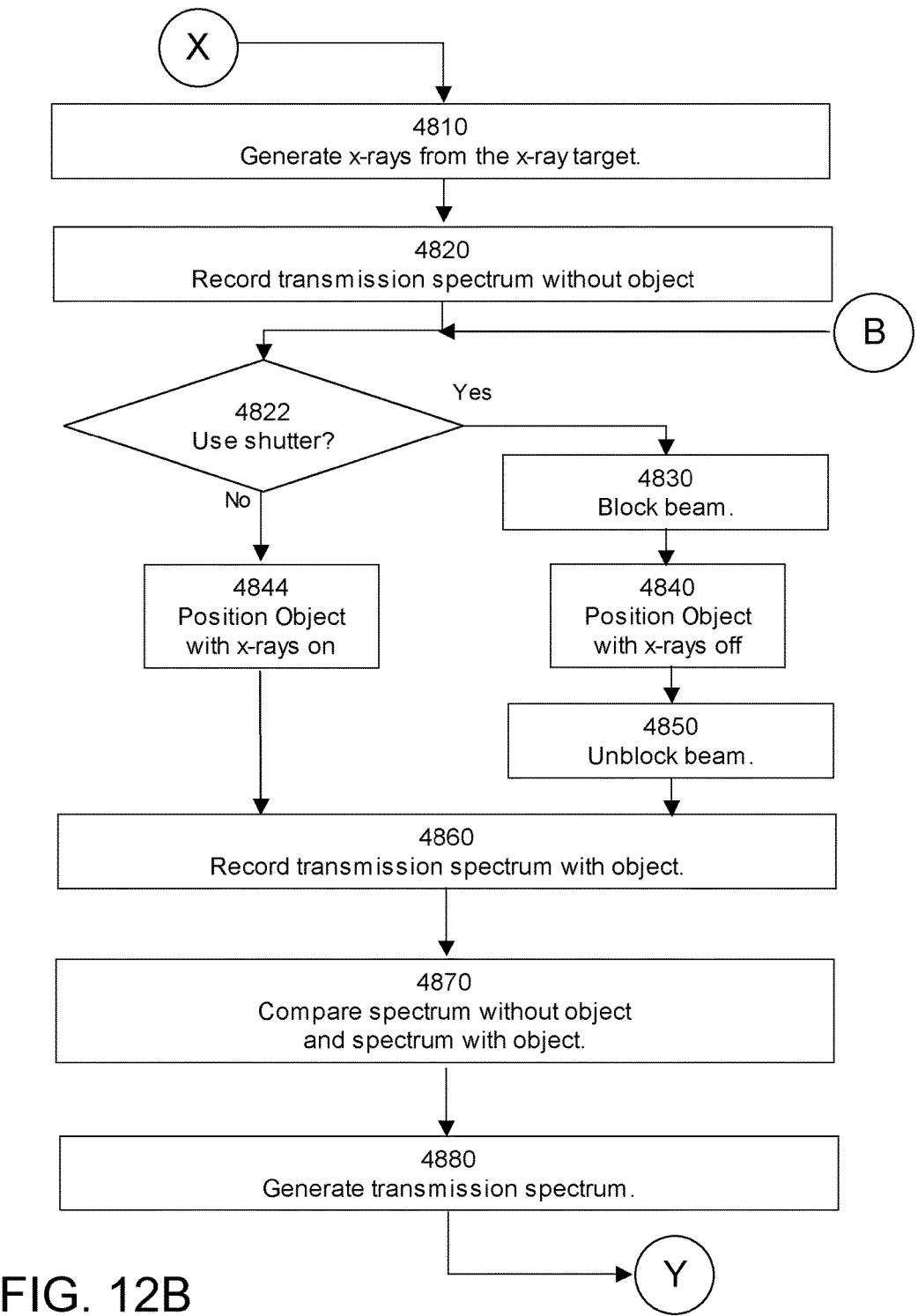
FIG. 12B presents the continuation of the steps of the method of FIG. 12A for collecting spectroscopy data according to an embodiment of the invention.
Figure 12C:
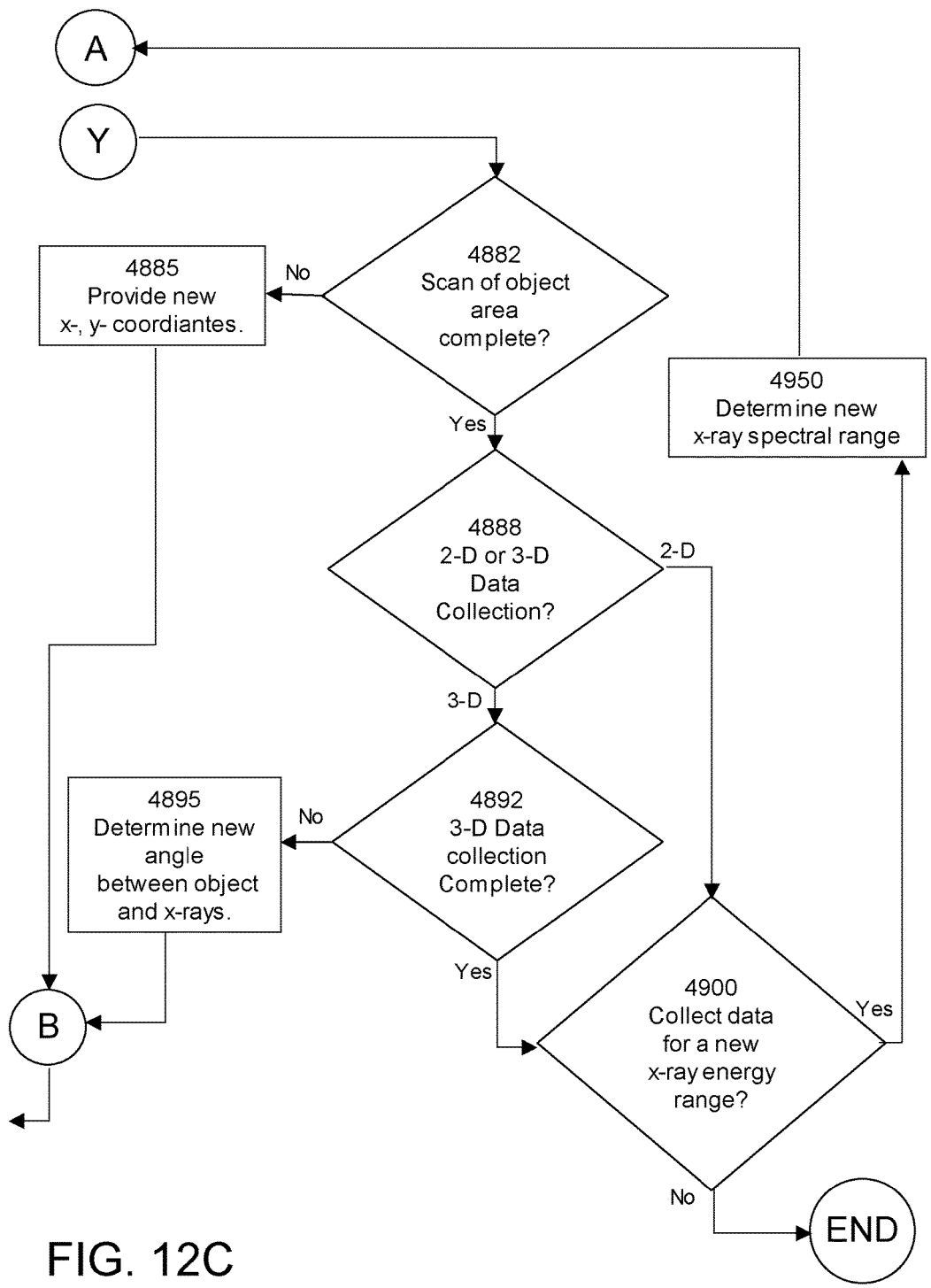
FIG. 12C presents the continuation of the steps of the method of FIGS. 12A and 12B for collecting spectroscopy data according to an embodiment of the invention.

The process steps to measure the transmission spectrum of an object according to an embodiment are represented in FIGS. 12A, 12B, and 12C, and are described below.

In the first step 4610 an object to be examined is selected, and the x-ray spectral range over which transmission information is desired is selected. The object may be any type of object, as long as a significant number of detectable x-rays are transmitted through the object.

In the next step 4620, an x-ray target that will produce x-rays in the spectral range when bombarded by electrons is selected. This may include a target with any number of x-ray generating materials that have been mentioned in the Patent Applications cited above, including tungsten, molybdenum, copper, rhodium, etc. The target may include a single x-ray generating material, or multiple x-ray generating materials, and may function in the x-ray source as a static or as a rotating anode.

In the next step 4630, a reflective x-ray focusing optic or optical system is selected that has a particular high-energy cutoff. This may arise from the material of the optic itself, reflective coating that have been applied to the optic or optical elements, or filters that are a part of the optical system.

The focusing optic will be designed to collect x-rays and focus them to a particular focal plane, and so in the next step 4640, the position in space where this focus plane will occur will be determined. This may be set by simply placing the optic into a predetermined position, or may require some alignment and adjustment of the position of the optic and the target within x-ray source, as noted in step 4660. Before this step is carried out, however, a decision step 4644 occurs, in which a decision is made as to whether an aperture or slit in the focal plane should be used. If the decision is yes, then a step 4650 in which the aperture or slit is positioned in the focal plane is carried out before the subsequent alignment step 4660.

Once the position of the x-rays in the focal plane (or the location of the aperture/slit) has been determined, the crystal analyzer is aligned to collect x-rays emerging from the focal plane (or aperture/slit, if used) and disperse them. The crystal analyzer may be any analyzer as described previously, including a single crystal structure, a mosaic crystal, etc.

In the next step 4680, the x-ray detector, generally a 2-D array detector as described above, will be placed to detect the x-rays dispersed by the crystal analyzer. This step will typically complete the alignment phase of the method, and the method proceeds to the steps shown in FIG. 12B, with the handoff designated by the circled X in the figures.

Referring now to FIG. 12B, in the next step 4810, the electrons bombard the target and x-rays are generated.

In the next step 4820, the transmission x-ray spectrum of the instrument (without the object in the optical path) is recorded. This serves as the reference data against which the subsequent measurements will be made.

In the following steps, the object will be positioned to be illuminated by x-rays. A decision 4822 to use or not use a shutter to block the beam made, and, if positive, the shutter is used to block the beam in step 4830, and in the next step 4840 the object may be positioned without the x-rays illuminating the object. Once positioned, the next step 4850 unblocks the x-ray beam, allowing the object to be illuminated by the x-rays. If the shutter is not used, then in step 4844 the object may be positioned while the x-rays beam is still on.

Once the x-rays illuminate the object, in the next step 4860 the x-rays transmitted through the object and then dispersed by the spectrometer are detected by the detector sensor and recorded.

Now that an x-ray transmission for the system with and without the object have been recorded, in the next step 4870 the two results may be compared, and the results of the comparison may be used to calculate the transmission spectrum of the object in the following step 4880. From the transmission results, the absorption spectrum of the object may also be inferred.

The transmission spectrum so generated represents the spectrum of the object at a single point of illumination in the object for a single x-ray bandwidth range (selected by the choice of optic and target in the previous steps). The method then proceeds to the next steps, represented by the circled Y in the FIGS. 12B and 12C, in which alternative variations of the data may be collected.

In the next step 4882, it is determined whether information about additional points in the object need be collected; i.e. is there a "scan" of the object desired that forms a "map" of the spectral properties of the object. If so, the new position coordinates for the object are provided in the next step 4885, and the path of control proceeds to the position marked with a circled B in FIG. 12C and back to FIG. 12B, where the process of steps 4822 4844, 4830, 4840, 4850, 4860, 4870, 4880 and 4882 are repeated in a loop until the entire desired areal dataset for the object has been completed.

If the dataset is complete, the next step 4888 determined whether the data collected will be a 2-D dataset (representing, for example, a planar "map" of the object) or if a 3-D representation of the object for analysis, using algorithms related to, for example, laminography or tomography, may be required. If 3-D data for this energy range is desired, the process determined in the next step 4892 whether in fact the 3-D data collection is complete. If not, the settings for a different relative rotational orientation for the object relative to the x-rays are determined in the next step 4895, and control proceeds to the position marked with a circled B in FIG. 12C and back to FIG. 12B, where the process of steps 4822 4844, 4830, 4840, 4850, 4860, 4870, 4880, 4882, 4885, 4888, 4892, and 4895 are repeated in a loop until the entire desired 3-D dataset for the object has been completed.

Once the 2-D and/or 3-D data collection has been completed, in the next step 4900 it is determined whether additional information for a different x-ray spectral range is required. If the collected dataset is adequate, the process ends. Data collection is complete.

If, on the other hand, additional spectral data is required, in the next step 4950 a new spectral range is determined, and control passes through the path marked with the circled A in FIG. 12C and back to FIG. 12A, where the process beginning with step 4620 repeats using the new spectral range.

Variations on the method described above may also be put into practice. For example, instead of first executing a loop of data collection in x- and y-dimensions at a fixed rotation position, and then changing the rotation setting to collect additional data, embodiments in which the object is rotated while the x- and y-position settings remain fixed may also be executed. Rotation of the object around the z-axis may also provide additional information that can be used in image tomosynthesis. Likewise, data for various spectral ranges may be collected with or without the completion of 2-D or 3-D scans.

7. Limitations and Extensions.

With this Application, several embodiments of the invention, including the best mode contemplated by the inventors, have been disclosed. It will be recognized that, while specific embodiments may be presented, elements discussed in detail only for some embodiments may also be applied to others. Also, details and various elements described as being in the prior art may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

Elements as shown in the drawings are meant to illustrate the functioning of various embodiments of the invention, and should not be assumed to have been drawn in proportion or to scale. Likewise, any single figure should not be construed as being an illustration showing all elements of any particular embodiment of the invention.

We claim:

1. A method for x-ray absorption spectroscopy by an x-ray optical system, comprising:
   collecting x-rays received from a first x-ray source through an x-ray optical system, the x-ray optical system having low-pass spectral filter properties such that x-rays above a cut-off energy are reduced;
   producing a focused x-ray beam by the x-ray optical system with a focus at a predetermined focal plane downstream of the x-ray optical system, the focused x-ray beam passing through a sample to be analyzed, the focused x-ray beam acting as a secondary source of diverging x-rays located at the focal plane; and
   receiving the diverging x-rays from the secondary source by an x-ray spectrometer having an x-ray wavelength dispersive element and an analyzer to analyze the spectrum of the dispersed x-rays.

2. The method of claim 1, wherein an aperture is placed at the focal plane and positioned to the said focused x-ray beam.

3. The method of claim 1, wherein the x-ray optical system comprises at least a reflective x-ray focusing optic.

4. The method of claim 3, wherein the reflective x-ray focusing optic has a predetermined high energy cutoff such that the x-ray reflectivity is less than 25% for x-rays with energies above 1.2 times a predetermined cutoff energy.

5. The method of claim 3, wherein at least a portion of a reflective surface of the reflective x-ray focusing optic is axially symmetric.

6. The method of claim 1, wherein the x-ray spectrometer comprises an array detector to record the x-rays dispersed by the x-ray wavelength dispersive element.

7. The method of claim 1, wherein the spectrometer is a Rowland circle geometry spectrometer.

8. The method of claim 1, wherein the spectrometer is a von Hamos spectrometer.

9. An x-ray absorption spectrometry system, comprising:
   an x-ray source;
   an x-ray optical system that receives x-rays from the x-ray source, includes a spectral filter property that reduces x-rays above a cut-off energy, and focuses the x-rays below the cut-off energy to a predetermined focal plane;
   a mount for receiving a sample and positioning the sample in a path of the focused x-ray beam;
   an aperture placed at the focal plane and centered with the focused x-ray beam in at least in one direction; and
   a x-ray spectrometer that receives the x-rays that pass through the aperture and analyzes the received x-rays.

10. The system of claim 9, wherein the focused x-ray beam has at least one dimension less than 30 micrometers.

11. The system of claim 9, wherein the x-ray optical system comprises at least a reflective x-ray mirror focusing optic with a surface, wherein a portion of the surface is cylindrically symmetric.

12. The system of claim 9, wherein the x-ray optical system comprises a reflective x-ray mirror focusing optic having a reflecting mirror surface, wherein a portion of the reflecting mirror surface has a quadric profile.

13. The system of claim 9, additionally comprising a beam stop to block a portion of the x-rays that are not focused by the x-ray optic.

14. The system of claim 9, wherein the x-ray spectrometer comprises an array detector.

15. The system of claim 9, wherein the x-ray spectrometer comprises a wavelength dispersive element comprising at least one crystal analyzer.

16. The system of claim 15, wherein the crystal analyzer comprises a single crystal.

17. The system of claim 15, wherein the crystal analyzer is curved with a predetermined radius.

18. The system of claim 15, wherein the crystal analyzer comprises a mosaic crystal.

19. The system of claim 15, wherein the x-ray spectrometer comprises a mechanism to rotate the x-ray wavelength dispersive element.

20. The system of claim 15, wherein the x-ray spectrometer includes a plurality of crystals, each of the crystals selected based on monochromaticity requirement.

21. The system of claim 9, wherein the mount receives one or more of a plurality of samples and positions at least one sample in the focused x-ray beam for analysis.

22. The system of claim 9 further comprising at least one x-ray shielding component that prevents x-rays not-dispersed by the wavelength dispersive component from arriving at the detector.

* * * * *

UNITED STATES PATENT AND TRADEMARK OFFICE
CERTIFICATE OF CORRECTION

PATENT NO. : 10,295,485 B2
APPLICATION NO. : 15/663831
DATED : May 21, 2019
INVENTOR(S) : Yun et al.

Page 1 of 1

It is certified that error appears in the above-identified patent and that said Letters Patent is hereby corrected as shown below:

On the Title Page

Column 1, and continued on Page 2, Items (63) and (60), under Related U.S. Application Data, should read as follows:
(63) Continuation-in-part of application No. 15/431,786, filed on Feb. 14, 2017, which is a continuation-in-part of application No. 15/269,855, filed on Sep. 19, 2016, now Pat. No. 9,570,265 and a continuation-in-part of application No. 15/166,274, filed on May 27, 2016, now Pat. No. 10,269,528, which is a continuation-in-part of application No. 14/999,147, filed on Apr. 1, 2016, now Pat. No. 9,543,109, which is continuation-in-part of application No. 14/490,672, filed Sep. 19, 2014, now Pat. No. 9,390,881, said application No. 15/269,855 is a continuation-in-part of application No. 15/544,191, filed Dec. 5, 2014, now Pat. No. 9,449,781 and a continuation-in-part of application No. 14/636,994, filed Mar. 3, 2015, now Pat. No. 9,448,190.

(60) Provisional application No. 62/117,062, filed on Feb. 17, 2015, provisional application No. 61/912,478, filed on Dec. 5, 2013, provisional application No. 61/912,486, filed on Dec. 5, 2013, provisional application No. 61/946,475, filed on Feb. 28, 2014, provisional application No. 62/008,856, filed on Jun. 6, 2014, provisional application No. 62/086,132, filed on Dec. 1, 2014, provisional application No. 61/880,151, filed Sep. 19, 2013, provisional application No. 61/894,073, filed Oct. 22, 2013, provisional application No. 61/931,519, filed Jan. 24, 2014, provisional application No. 62/141,847, filed Apr. 1, 2015, provisional application No. 62/155,449, filed Apr. 30, 2015.

Signed and Sealed this
Third Day of September, 2019

Andrei Iancu
*Director of the United States Patent and Trademark Office*